United States Patent
Frasier et al.

(10) Patent No.: US 8,888,819 B2
(45) Date of Patent: Nov. 18, 2014

(54) CONNECTOR FOR SECURING AN OFFSET SPINAL FIXATION ELEMENT

(75) Inventors: William J. Frasier, New Bedford, MA (US); Nicholas Pavento, Marlboro, MA (US); Sara Dziedzic, North Attleboro, MA (US); Tina Easterbrooks, Plainville, MA (US); Michael Mahoney, Middletown, RI (US); Shawn D. Stad, Fall River, MA (US)

(73) Assignee: Depuy Synthes Products, LLC, Raynham, MA (US)

( * ) Notice: Subject to any disclaimer, the term of this patent is extended or adjusted under 35 U.S.C. 154(b) by 1348 days.

(21) Appl. No.: 11/897,572

(22) Filed: Aug. 31, 2007

(65) Prior Publication Data
US 2009/0062860 A1 Mar. 5, 2009

(51) Int. Cl.
*A61B 17/70* (2006.01)
*A61B 19/00* (2006.01)

(52) U.S. Cl.
CPC ......... *A61B 17/7041* (2013.01); *A61B 17/7076* (2013.01); *A61B 17/7035* (2013.01); *A61B 2019/307* (2013.01); *A61B 17/701* (2013.01); *A61B 17/7086* (2013.01); *A61B 17/7037* (2013.01)
USPC ........................................... 606/264; 606/276

(58) Field of Classification Search
CPC ................. A61B 17/7034; A61B 17/7041
USPC ................ 606/264–267, 270, 272, 86 A
See application file for complete search history.

(56) References Cited

U.S. PATENT DOCUMENTS

| | | | | |
|---|---|---|---|---|
| 5,776,135 A * | 7/1998 | Errico et al. | ................. | 606/266 |
| 6,063,089 A * | 5/2000 | Errico et al. | ................. | 606/278 |
| 6,261,288 B1* | 7/2001 | Jackson | ........................ | 606/250 |
| 6,726,692 B2* | 4/2004 | Bette | .............................. | 606/99 |
| 8,298,269 B2* | 10/2012 | Null et al. | ..................... | 606/267 |
| 2002/0169450 A1* | 11/2002 | Lange | .............................. | 606/61 |
| 2002/0173789 A1* | 11/2002 | Howland | ......................... | 606/61 |
| 2003/0171755 A1* | 9/2003 | Moseley et al. | ................. | 606/73 |
| 2004/0210216 A1* | 10/2004 | Farris et al. | ..................... | 606/61 |
| 2005/0010216 A1* | 1/2005 | Gradel et al. | ................... | 606/61 |
| 2005/0101956 A1* | 5/2005 | Simonson | ...................... | 606/61 |
| 2005/0228382 A1* | 10/2005 | Richelsoph et al. | ............ | 606/61 |
| 2005/0245928 A1* | 11/2005 | Colleran et al. | ............... | 606/61 |
| 2006/0111730 A1* | 5/2006 | Hay | .............................. | 606/104 |
| 2006/0116676 A1* | 6/2006 | Gradel et al. | ................... | 606/61 |
| 2007/0270810 A1* | 11/2007 | Sanders | ........................ | 606/61 |
| 2007/0276367 A1* | 11/2007 | Puno | .............................. | 606/61 |
| 2008/0109039 A1* | 5/2008 | Michielli et al. | .............. | 606/251 |
| 2008/0208257 A1* | 8/2008 | Matthys | ........................ | 606/278 |
| 2010/0094346 A1* | 4/2010 | Matityahu | ..................... | 606/250 |
| 2010/0094349 A1* | 4/2010 | Hammer et al. | .............. | 606/264 |
| 2010/0198260 A1* | 8/2010 | Gabelberger et al. | ......... | 606/264 |
| 2010/0268279 A1* | 10/2010 | Gabelberger et al. | ......... | 606/278 |

* cited by examiner

*Primary Examiner* — Ellen C Hammond
(74) *Attorney, Agent, or Firm* — Nelson Mullins Riley & Scarborough LLP

(57) ABSTRACT

The present invention provides an implant that can be inserted on top of a previously placed spinal fixation element. The implant includes a bone anchor and a connector body. The bone anchor includes a proximal head and a distal shaft extending along a longitudinal axis configured to engage bone. The connector body is configured to engage the proximal head of bone anchor and engage a spinal fixation element offset from longitudinal axis of the bone anchor shaft. Because, the implant is inserted over the spinal fixation element, direct visualization of the surgical site is available during insertion. In addition, the implant may provide tactile or audible feedback indicating that the spinal fixation element has been engaged by the implant.

10 Claims, 23 Drawing Sheets

CONNECTOR FOR SECURING AN OFFSET SPINAL FIXATION ELEMENT

FIELD OF INTEREST

The present invention relates to connector devices and methods for use during orthopedic surgery. More particularly, the present invention relates to implants for securing previously inserted spinal fixation elements using bone anchors placed adjacent to the spinal fixation elements (SFE).

BACKGROUND

For a number of known reasons, spinal fixation devices are used in orthopedic surgery to align and/or fix a desired relationship between adjacent vertebral bodies. Such devices typically include a spinal fixation element, such as a relatively rigid fixation rod, that is coupled to adjacent vertebrae by attaching the element to various anchoring devices, such as hooks, bolts, wires, or screws. The fixation elements can have a predetermined contour that has been designed according to the properties of the target implantation site, and once installed, the instrument holds the vertebrae in a desired spatial relationship, either until desired healing or spinal fusion has taken place, or for some longer period of time.

Spinal fixation elements can be anchored to specific portions of the vertebrae. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a head portion having a rod-receiving element, usually in the form of a U-shaped slot formed in the head. A set-screw, plug, or similar type of fastening mechanism is used to lock the fixation element, e.g. a rod, into the rod-receiving head of the pedicle screw. In use, the shank portion of each screw is threaded into a vertebra, and once properly positioned, a rod is seated through the rod-receiving member of each screw and the rod is locked in place by tightening a cap or other fastener mechanism to securely interconnect each screw and the fixation rod.

Recently, the trend in spinal surgery has been moving toward providing minimally invasive elements and methods for implanting spinal fixation devices. For example, one such method, a rod-first method, includes inserting a spinal rod through a first incision and positioning the spinal rod along a patient's spinal column adjacent to one or more vertebra. After the spinal rod is inserted, a first bone anchor is inserted through the first bone anchor incision or through a separate incision, and then additional bone anchors are inserted each through a separate incision along the spinal rod. After a bone anchor is inserted and anchored in bone it is coupled to the spinal rod. A rod-first method is a minimally invasive technique in which the bone anchors are inserted after the rod and adjacent to the rod, as opposed to a conventional surgical technique in which the bone anchors are inserted first then the rod is placed in rod-receiving elements lying over the heads of the bone anchors.

However, such minimally invasive procedures, such as rod first techniques, introduce other issues. Because the bone anchors are inserted percutaneously after the spinal fixation element and adjacent to the spinal fixation element, connecting the bone anchors to the spinal fixation element can be difficult because the surrounding tissue and muscle may obstruct a direct view of the surgical site. Thus, what is needed when using minimally invasive surgical procedures, such as rod first techniques is a means for being able to engage a previously inserted spinal fixation element with an implant at a sub facial surgical site.

SUMMARY

Embodiments of the present invention provide an implant that can be inserted on top of a previously placed spinal fixation element. Because, the implant is inserted over the spinal fixation element, direct visualization of the surgical site is available during insertion. In addition, the implant may provide tactile or audible feedback indicating that the spinal fixation element has been engaged by the implant.

In accordance with a first aspect, an implant is provided for use in a minimally invasive rod first spinal fixation. The implant includes a bone anchor and a connector body. The bone anchor includes a proximal head and a distal shaft extending along a longitudinal axis configured to engage bone. The connector body is configured to engage the proximal head of bone anchor and engage a spinal fixation element offset from longitudinal axis of the bone anchor shaft.

In one embodiment, the connector body may include a cavity for receiving the proximal head of the bone anchor and a hook for receiving the spinal fixation element. The hook may be deformable or include spring loaded fingers for engaging the spinal fixation element.

In another embodiment, the connector body may include a lower clamp mechanism and an upper clamp mechanism configured to mate with the lower clamp mechanism to engage the spinal fixation device.

In another embodiment, the connector body is configured to engage the spinal fixation element which is configured to secure the proximal head of the bone anchor. The connector body includes first and second halves. The first half is configured to engage the proximal head of the bone anchor and seat the spinal fixation element. The second half is configured to mate with the first half to capture the spinal fixation element. Capturing the spinal fixation element secures the connector body on the bone anchor.

In another embodiment, an engagement tool is provided for engaging the spinal fixation device with connector body. The engagement tool includes an outer sleeve and an inner plunger. The outer sleeve has a proximal end, a distal end configured to engage the spinal fixation element, and a lumen extending between the proximal and distal ends. The inner plunger is configured to fit inside the outer sleeve and engage the connector body. In operation, when the inner plunger is inserted into the outer sleeve to engage the connector body, the plunger causes the connector body to engage the spinal fixation element engaged by the outer sleeve.

In accordance with another aspect, a method is provided for securing a previously inserted spinal fixation element. The method uses the implant described above. First the implant is inserted at the surgical site. Once inserted, the spinal fixation element may be engaged by the connector body of the implant.

BRIEF DESCRIPTION OF THE FIGURES

These and other features and advantages of the devices and methods disclosed herein will be more fully understood by reference to the following detailed description in conjunction with the attached drawings in which like reference numerals refer to like elements through the different views. The drawings illustrate principles of the instruments and methods disclosed herein and, although not to scale, show relative dimensions.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Exemplary embodiments described herein concern implants for securing spinal fixation elements and methods of use. As such, exemplary embodiments of implants are formed of suitable materials for use in a human body. Suitable materials include, but are not limited to, stainless steel, titanium, or the like. Exemplary embodiments of implants are particularly suited for use in rod-first spinal surgical techniques. An exemplary embodiment of an implant secures the previously inserted spinal fixation element. Exemplary embodiments of implants are sized and dimensioned for insertion through a minimally invasive surgical access port, such as a cannula. Additionally, exemplary embodiments of implants are configured for use in a rod-first surgical technique in which an SFE is inserted and positioned in a patient before insertion of the implant, and in which the bone anchors are positioned adjacent to an SFE and not beneath the SFE.

Figure 1:
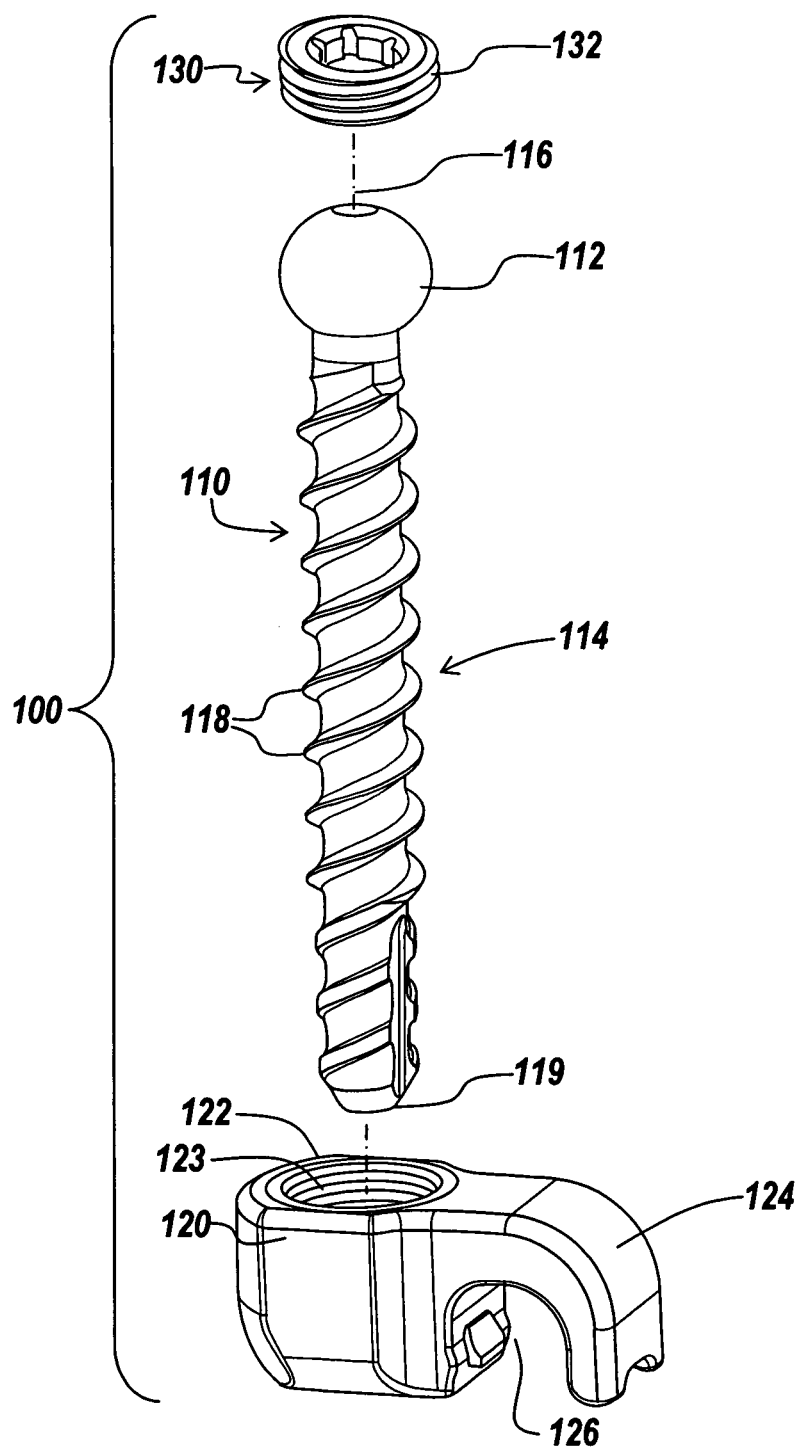
FIG. 1 illustrates an exemplary embodiment of an implant.

FIG. 1 is an exploded view of an embodiment of an implant 100. Here the implant includes a bone anchor 110, and a connector body 120. In certain embodiments, the system further includes one or more locking mechanism 130.

The bone anchor 110 comprises a joint portion, illustrated as a proximal anchor head 112, for coupling the bone anchor 110 to the connector body 120, and an anchoring portion, illustrated as a distal shaft 114 configured to engage bone. The distal shaft 114 of the bone anchor 110 extends along a longitudinal axis 116. The distal shaft 114 may include one or more bone engagement mechanisms to facilitate gripping engagement of the bone anchor to bone. In the illustrated embodiment, the distal shaft 114 includes an external thread 118 extending along at least a portion of the shaft for engaging bone. In the illustrated embodiment, the external thread 118 is a single lead thread that extends from a distal tip 119 of the shaft to the anchor head 112, though one skilled in the art will recognize that the external thread may extend along any selected portion of the shaft and have any suitable number of leads. Other suitable bone engagement mechanisms include, but are not limited to, one or more annular ridges, multiple threads, dual lead threads, variable pitched threads and/or any conventional bone engagement mechanism.

The anchor head 112 of the bone anchor 110 may be configured to facilitate adjustment of the bone anchor 110 relative to the connector body 120 of the implant 110. For example, the illustrative anchor head 112 may be substantially spherical to permit pivoting of the bone anchor 110 relative to the connector body 120 in one or more selected directions. In some embodiments, the anchor head 112 may also have surface texturing, knurling and/or ridges.

In this example, the connector body includes a cavity 122 and a hook 124. The cavity passes through the connector body 120 and is configured for receiving the bone anchor 110 and engaging the proximal head 112 of the bone anchor 110. The hook 124 defines a slot 126 for engaging a spinal fixation element, such as a rod (not shown) that is offset from the longitudinal axis of the distal shaft 114 of the bone anchor 110.

The connector body 120 receives the proximal head 112 of the bone anchor in the cavity 122 to couple the bone anchor 110 thereto. The connector body 120 receives a spinal fixation element in the slot 126 defined by the hook 124, thereby coupling the spinal fixation element engaged by the connector body 120 to the bone anchor 110.

The cavity 122 of the connector body 120 is configured to interact with the spherical shape of the proximal head 112 of the bone anchor 110 to allow the bone anchor 110 to rotate and pivot independently of the connector body 120. Likewise, once the distal shaft 114 of the bone anchor 110 has been implanted in a bone (not shown) the interaction of the cavity 122 and proximal head 112 allow the connector body 120 to be positioned to engage a spinal fixation element (not shown).

Once, the connector body 120 has been appropriately positioned, a locking member 130 may be used to secure or otherwise "fix" the position of the connector body. In the embodiment of FIG. 1, the locking member 130 is a set screw. The set screw 130 has external threads 132 configured to engage internal threads 123 in the cavity of the connector body 120. The set screw 130 is inserted into the cavity 122 and engages the proximal head 112 of the bone anchor 110 to secure the positions of the bone anchor 110 and connector body 120 in relation to each other.

In certain embodiments, the locking mechanism 130 may also function to secure or other wise "fix" a spinal fixation element engaged by the connector body 120. In some such embodiments, the locking mechanism may work in conjunction with a securing mechanism to secure the connector body 120 and spinal fixation element. In other embodiments, a second locking mechanism may be provided to secure or otherwise "fix" the spinal fixation device engaged by the connector body.

Figure 2A:
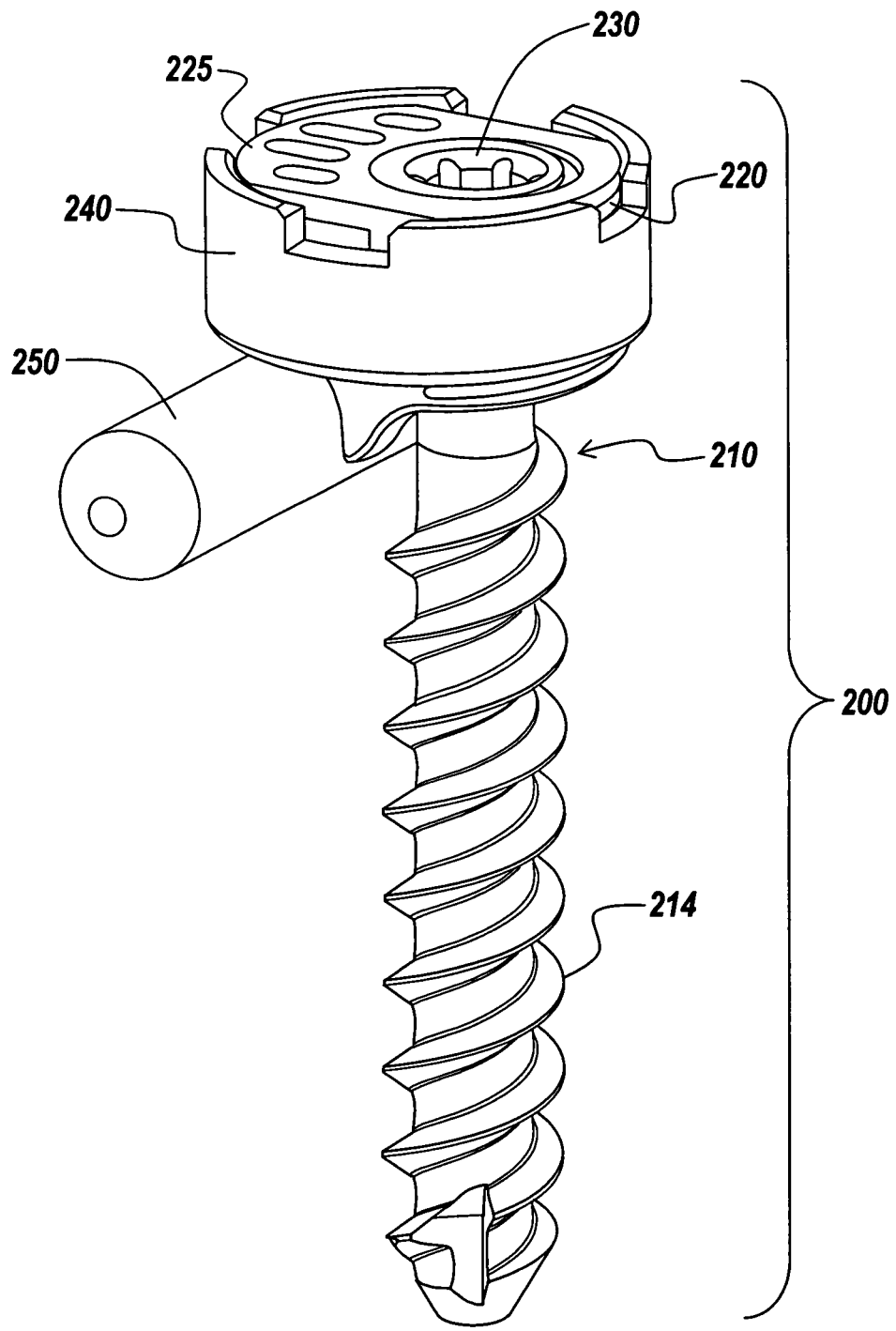
FIGS. 2A-2B illustrate another exemplary embodiment of an implant.
Figure 2B:
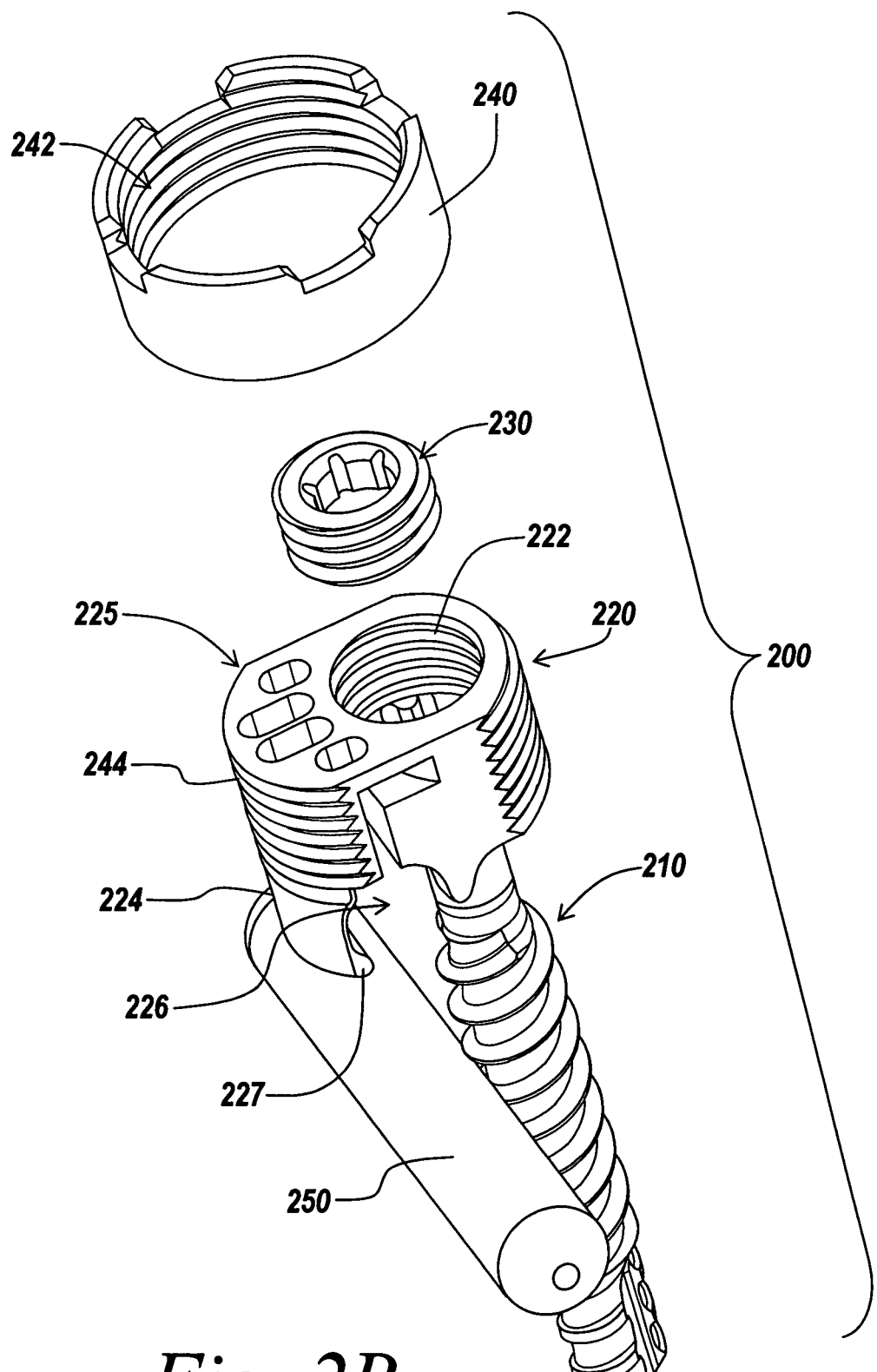

FIGS. 2A and 2B depict another embodiment of an implant 200 for securing a spinal fixation element. FIG. 2A depicts the implant 200 assembled and engaging a spinal fixation device 250, in this case a spinal rod. FIG. 2B depicts an exploded view of the implant 200.

In the embodiment of FIGS. 2A and 2B, the implant 200 has a bone anchor 210 and a connector body 220 configured to engage the bone anchor 210 and spinal fixation element 250. In the example depicted in FIGS. 2A and 2B, the bone anchor 210 and connector body 220 are already assembled such that the proximal head of the bone anchor 210 is engaged by the cavity 222 of the connector body 220, leaving only the distal shaft 214 of the bone anchor 210 visible. The implant 200 also includes a first locking mechanism 230 and a second locking mechanism 240.

In this embodiment, the connector body 220 includes cavity 222 for receiving the bone anchor 210 and first locking mechanism 230 as well a hook 224 defining a slot 226 for receiving the spinal fixation element 250 that is offset from the longitudinal axis of the distal shaft 214 of the bone anchor 210.

In this embodiment, the implant is configured to be top-loaded so as to engage the spinal fixation element 250 from above. The bone anchor 210 is implanted adjacent to the spinal fixation element 250 so that the spinal fixation element 250 is offset from the longitudinal axis of the distal shaft 214 of the bone anchor 210. The connector body 220 is able to move polyaxially with respect to the bone anchor 210 to engage the spinal fixation element 250.

The hook 224 of connector body 220 may also include leaf spring features 225 and surface configurations 227. The leaf spring features allow the hook 224 to deform or flex outward around the spinal fixation element 250 and then snap onto the spinal fixation element 250 thereby engaging the spinal fixation element 250 in slot 226. The surface configurations 227 include a lip on the hook 224 that push the hook 224 outward while the spinal fixation element 250 is inserted into the slot 226 and contains the spinal fixation element 250 after insertion. This snap-on feature also provides the benefit of giving the user tactile and audible feedback that the spinal fixation element 250 has been engaged. It should be apparent that this snap-on connection is but one possible method of engaging the spinal fixation element. Other possible implementations and embodiments will be apparent to one skilled in the art given the benefit of this disclosure.

Once the spinal fixation element 250 has been engaged by the connector body 220, the polyaxial motion of the connector body 220 is fixed using the first locking mechanism 230. In this example, the first locking mechanism 230 is a set screw configured to engage the bone anchor 210 and connector body 220 to lock their positions relative to each other. The set screw 230 inserted into the cavity 222 of the connector body 220 can be seen in FIG. 2A.

The embodiment of FIGS. 2A and 2B further includes a second locking mechanism 240. In this example, the second locking mechanism 240 is an outer ring. The outer ring 240 includes a tapered inner thread 242 configured to engage an outer thread 244 on the connector body 220. When the outer ring 240 is placed on the connector body 220 the tapered thread 242 constricts the hook 224 locking the spinal fixation element 250 inside the slot 226. The outer ring 240 installed on the connector body 220 can be seen in FIG. 2A. It should be understood that the outer ring 240 is but one possible implementation of a mechanism for securing the spinal fixation element 250. Other possible implementations and embodiments will be apparent to one skilled in the art given the benefit of this disclosure.

Figure 3A:
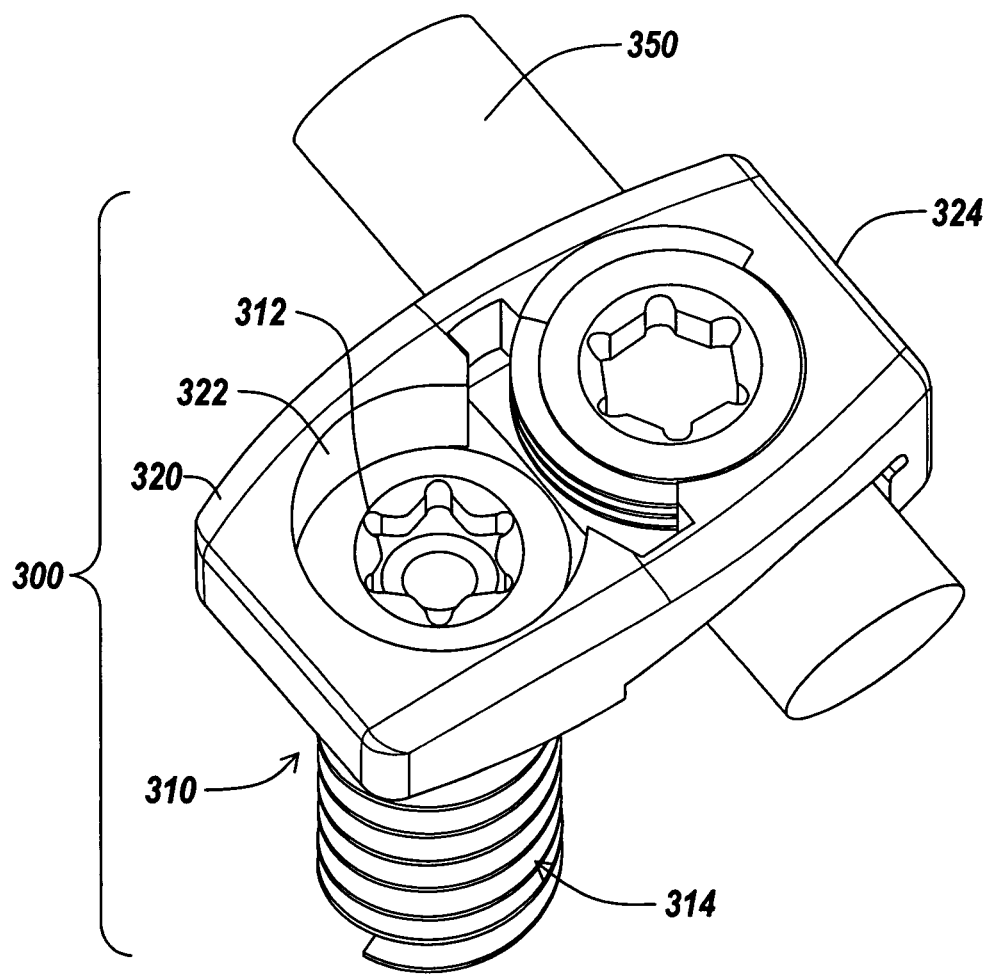
FIGS. 3A-3C illustrate another exemplary embodiment of an implant.
Figure 3B:
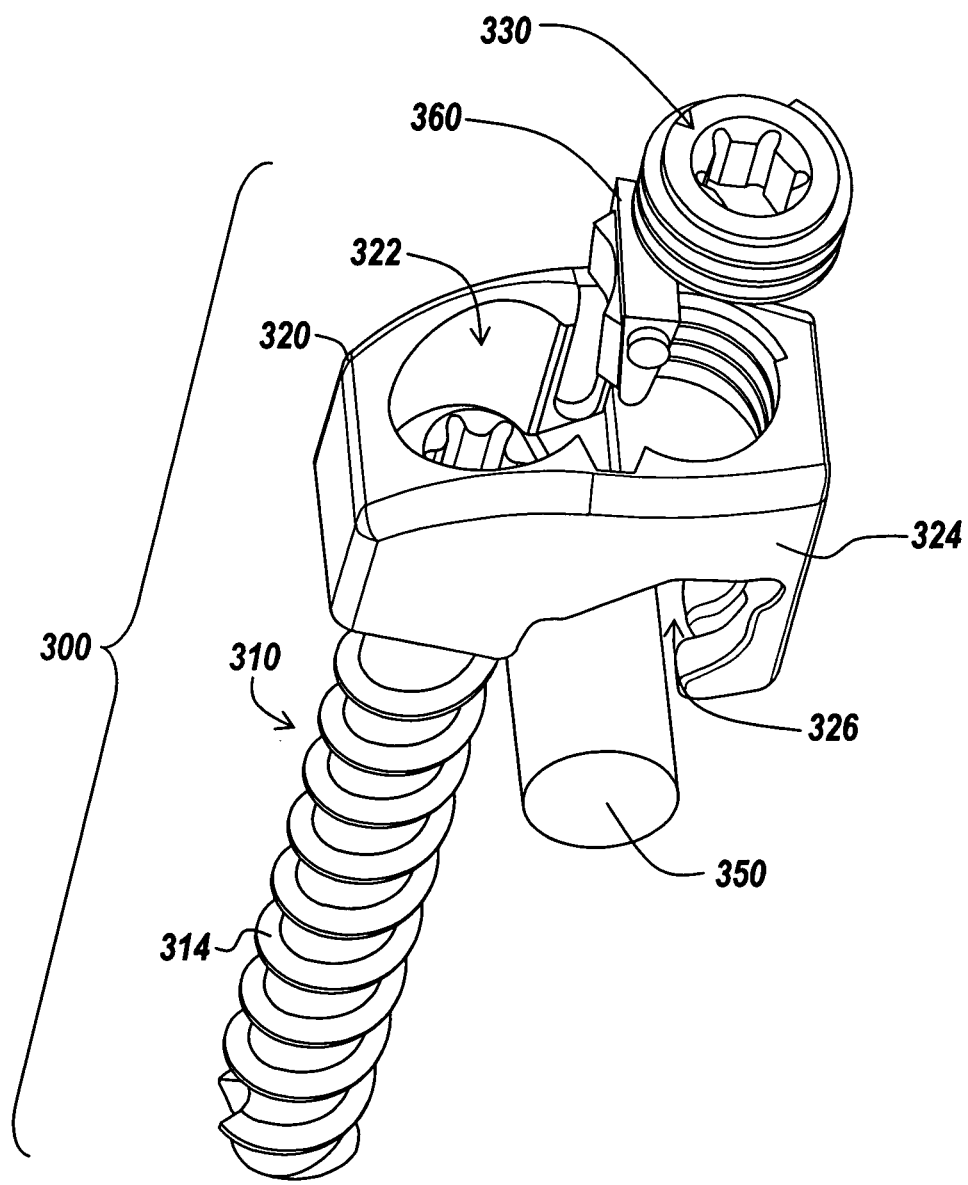
Figure 3C:
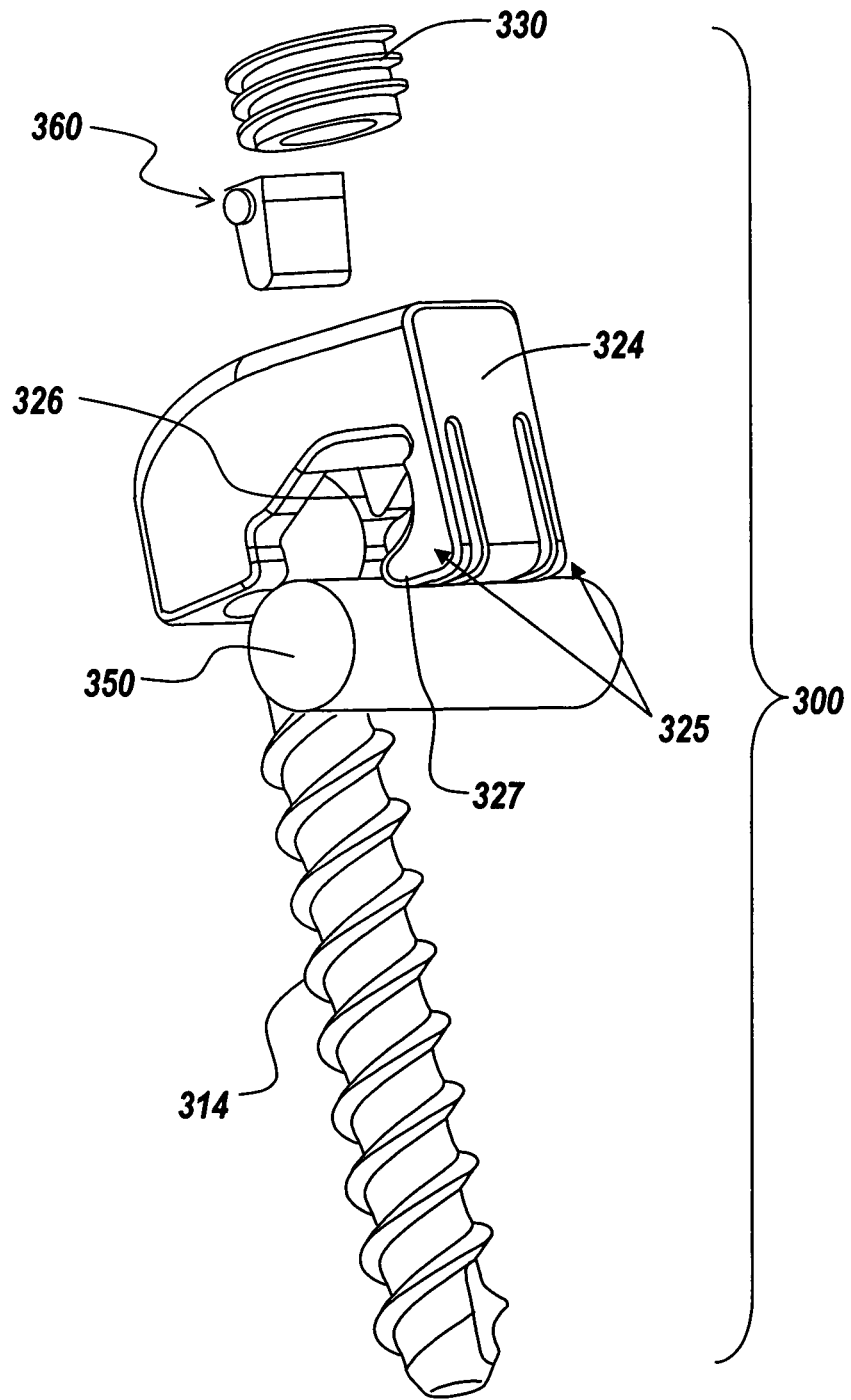

Another embodiment of an implant 300 can be seen in FIGS. 3A-3C. In this embodiment the implant 300 has a bone anchor 310 and a connector body 320 configured to engage the bone anchor 310 and spinal fixation element 350. As with FIGS. 2A and 2B, the bone anchor 310 and connector body 320 are already assembled such that the proximal head 312 of the bone anchor 310 is engaged by the cavity 322 of the connector body 320. In this embodiment, the implant 300 further includes a first locking mechanism 330 and a securing mechanism 360. Allowing the implant to be introduced fully assembled reduces the steps for the surgeon in the procedure. This is especially advantageous in minimally invasive procedures where secondary locking mechanism introductions are more difficult.

In this embodiment, the connector body 320 includes a cavity 322 for receiving the bone anchor 310, locking mechanism 330, and securing mechanism 360 as well as a hook 324 defining a slot 326 for receiving the spinal fixation element 350 that is offset from the longitudinal axis of the distal shaft 314 of the bone anchor 310. In this embodiment, the cavity 322 is configured to receive the locking mechanism 330 adjacent to, rather than on top of the proximal head 312 of the bone anchor 310 and on top of the securing mechanism 360.

The implant is configured to be top-loaded completely assembled so as to engage the spinal fixation element 350 from above. The bone anchor 310 is implanted adjacent to the spinal fixation element 350 so that the spinal fixation element 350 is offset from the longitudinal axis of the distal shaft 314 of the bone anchor 310. The connector body 320 is able move polyaxially with respect to the bone anchor to engage the spinal fixation element 350.

The hook 324 of connector body 320 may also include spring loaded fingers 325 with surface configurations 327. The spring loaded fingers 325 deform or flex outward around the spinal fixation element 350 and then snap onto the spinal fixation element 350 thereby engaging the spinal fixation element 350 in slot 326. The surface configurations 327 include a lip on the fingers 325 that push the fingers 325 outward while the spinal fixation element 350 is inserted into the slot 326 and contains the spinal fixation element 350 after insertion. This snap-on feature also provides the benefit of giving the user tactile and audible feedback that the spinal fixation element 350 has been engaged.

Once the spinal fixation element 350 has been engaged by the connector body 320 the locking mechanism 330, in this case a set screw, may be advanced. In this embodiment, the set screw 330 works in conjunction with a securing mechanism 360 to secure both the polyaxial motion of the connector body 320 and the spinal fixation element 350. In this example, the securing mechanism 360 is a wedge contoured to mate with both the proximal head 312 of the bone anchor 310 and the spinal fixation element 350. As the set screw 330 is advanced, the wedge 360 is advanced which in turn pushes the proximal head 312 against one side of the connector body 320 and the spinal fixation element 350 against the other side of the connector body 320 securing the position of the connector body 320 and the spinal fixation element 350.

Figure 4A:
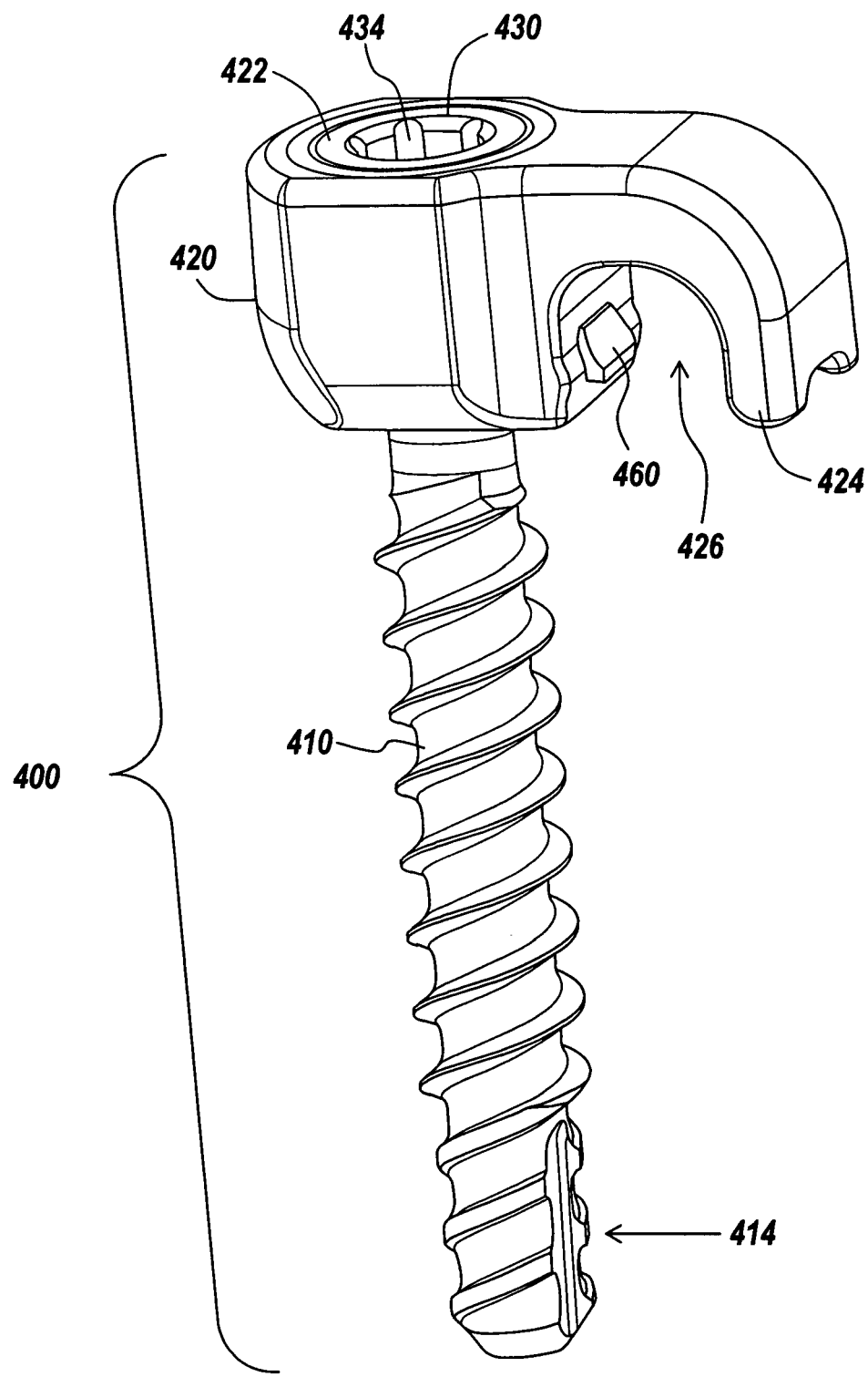
FIGS. 4A-4C illustrate another exemplary embodiment of an implant.
Figure 4B:
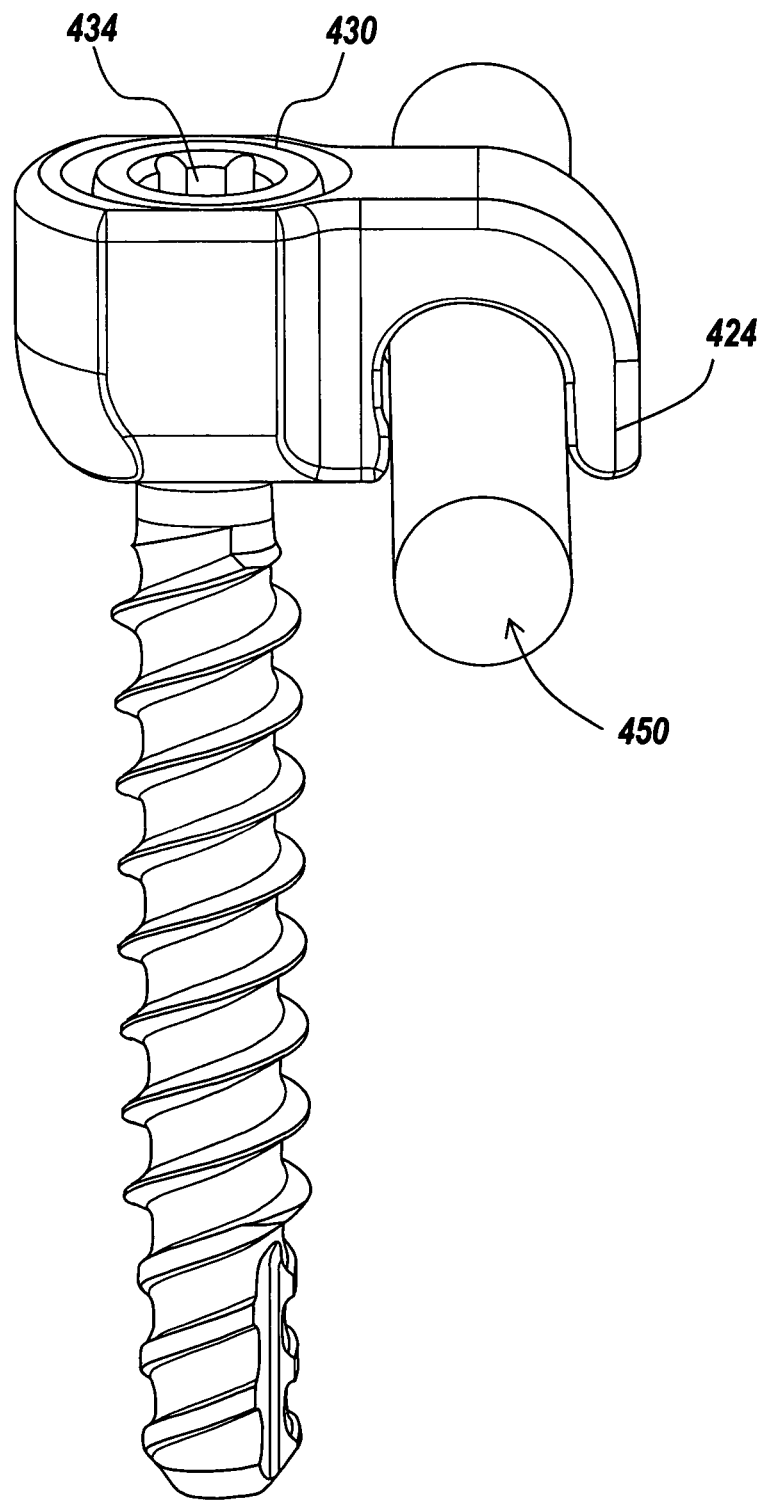
Figure 4C:
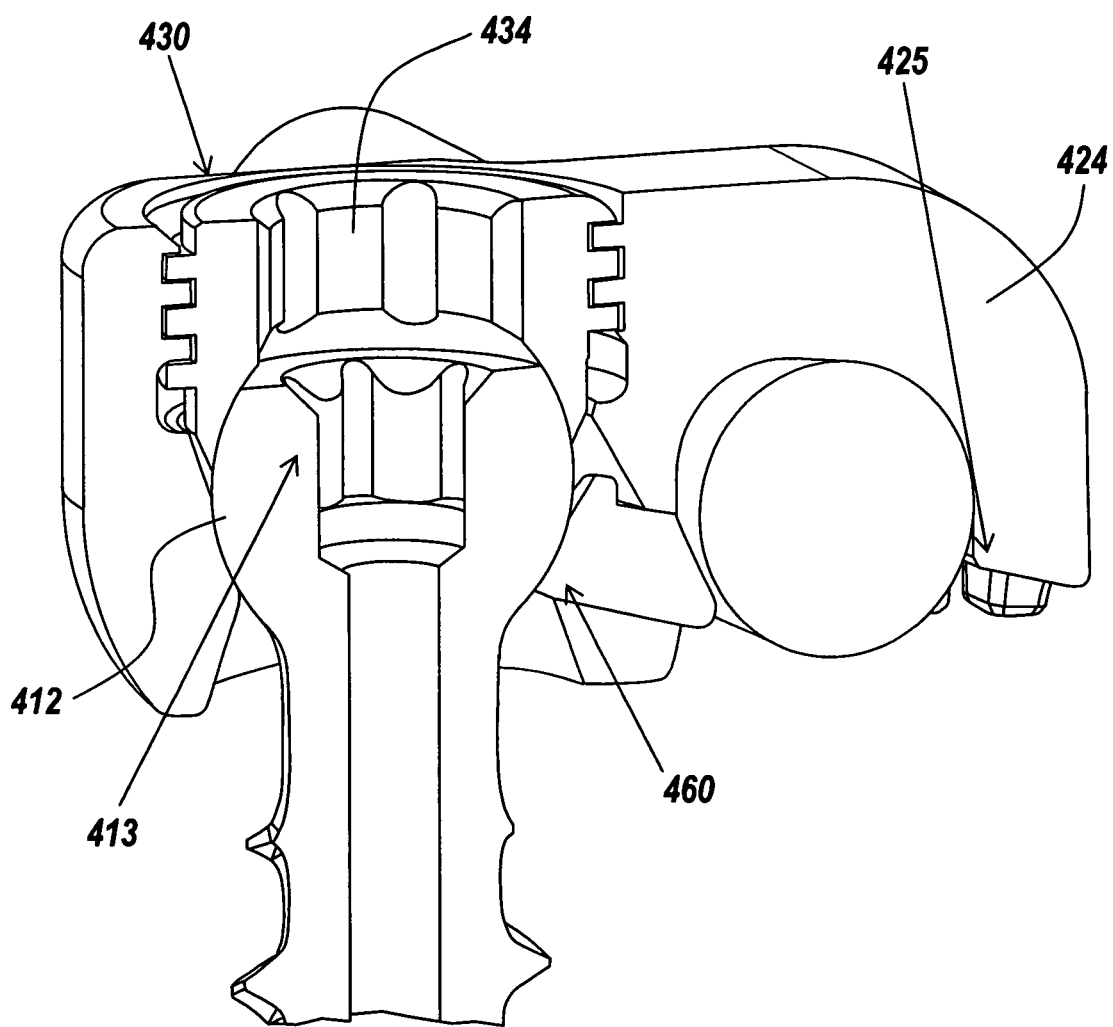

Another embodiment of an implant 400 can be seen in FIGS. 4A-4C. As with the previous embodiments, in this embodiment the implant 400 has a bone anchor 410 and a connector body 420 configured to engage the bone anchor 410 and spinal fixation element 450. In this embodiment, the implant 400 further includes a first locking mechanism 430 and an integrated securing mechanism 460.

In this embodiment, the connector body 420 includes a cavity 422 for receiving the bone anchor 410 and locking mechanism 430 as well a hook 424 defining a slot 426 for receiving the spinal fixation element 450 that is offset from the longitudinal axis of the distal shaft 414 of the bone anchor 410. In this embodiment, the securing mechanism 460 is integrated into the connector body 420.

The implant is configured to be top-loaded completely assembled with the locking mechanism 430 preloaded or inserted separately. In this embodiment, the locking mechanism has a pass through feature 434 allowing the bone anchor 410 to be implanted while the locking mechanism is inserted in the connector body 420. The bone anchor 410 is implanted adjacent to the spinal fixation element 450 so that the spinal fixation element 450 is offset from the longitudinal axis of the distal shaft 414 of the bone anchor 410. The connector body 420 is able to move polyaxially with respect to the bone anchor to engage the spinal fixation element 450.

The hook 424 of connector body 420 may also include one or more snap on features 425. The hook 424 is capable of deforming or flexing outward around the spinal fixation element 450 and then snap onto the spinal fixation element 450 with the snap on features 425 thereby engaging the spinal fixation element 450 in slot 426. The snap-on features 425 also provides the benefit of giving the user tactile and audible feedback that the spinal fixation element 450 has been engaged.

Once the spinal fixation element 450 has been engaged by the connector body 420 the locking mechanism 430, in this case a set screw, may be advanced. In this embodiment, the set screw 430 works in conjunction with a securing mechanism 460 to fix secure both the polyaxial motion of the connector body 420 and the spinal fixation element 450. The securing mechanism is configured to engage both the proximal head 412 and the spinal fixation element 450. As the set screw 430 is advanced, the set screw pushes the proximal head 412 against the securing mechanism 460 locking the polyaxial motion of the connector body 420. The proximal head 412 pushes the securing mechanism 460 against the spinal fixation element 450. The securing mechanism 460 pushes the spinal fixation element 450 against the hook 424 securing the position of the spinal fixation element 450.

In the embodiment of FIGS. 4A-4C, the set screw 430 further includes a pass-through feature 434. The pass through feature 434 allows an insertion tool to access the bone anchor drive feature 413 of the bone anchor 410 with the set screw 430 in place. This allows the height of the bone anchor 410 to be adjusted after the bone anchor has been implanted and the SFE has been captured.

FIGS. 5A-5E depict the use of an instrument 500 for assisting in the engagement of the spinal fixation element 350 by an implant 300. In the example of FIGS. 5A-5E, the instrument 500 is used with the embodiment of the implant 300 set forth in FIG. 3 but is usable with any of the embodiments of implants describe above. The instrument 500 includes a sleeve 510 and a plunger 530.

Figure 5A:
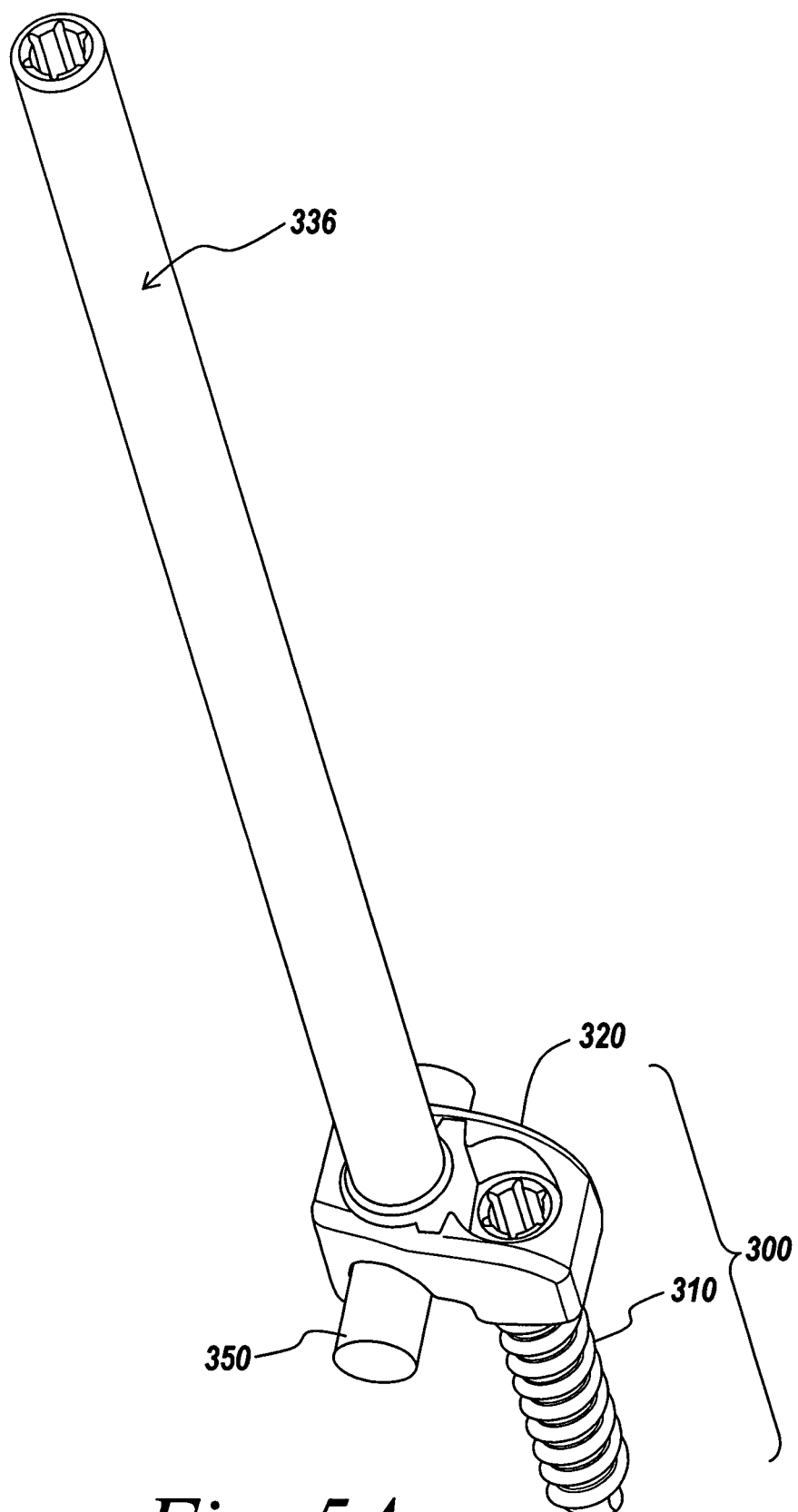
FIGS. 5A-5E illustrate an exemplary embodiment of an instrument for engaging a spinal fixation element with an implant.

In FIG. 5A, the implant 300 has been implanted at a surgical site. In this example, an extension shaft 336 extends from the locking mechanism 330. The extension shaft 336 may be used to place the implant and/or drive the locking mechanism 330. In certain embodiments, the extension shaft may include a break-away feature for removal after the connector body 320 and spinal fixation element 350 have been secured.

Figure 5B:
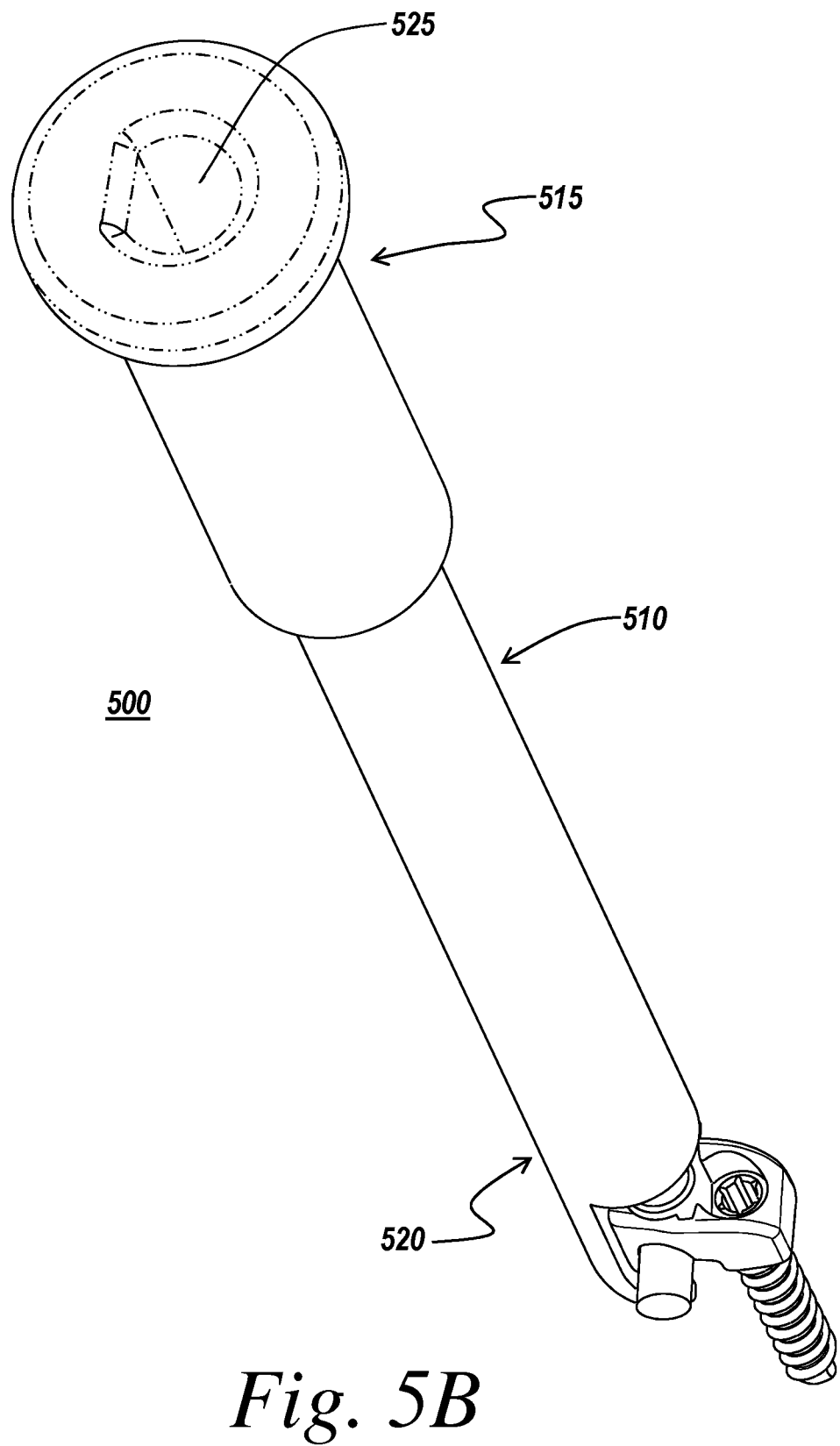

In FIG. 5B, the sleeve 510 of the instrument 500 has been inserted over the extension shaft 336. The sleeve 510 has a proximal end 515, a distal end 520 and a lumen 525 extending between the proximal 515 and distal 520 ends. The distal end 520 is configured to engage the spinal fixation element 350. A close-up of the distal end 520 can be seen in FIG. 5C.

Figure 5C:
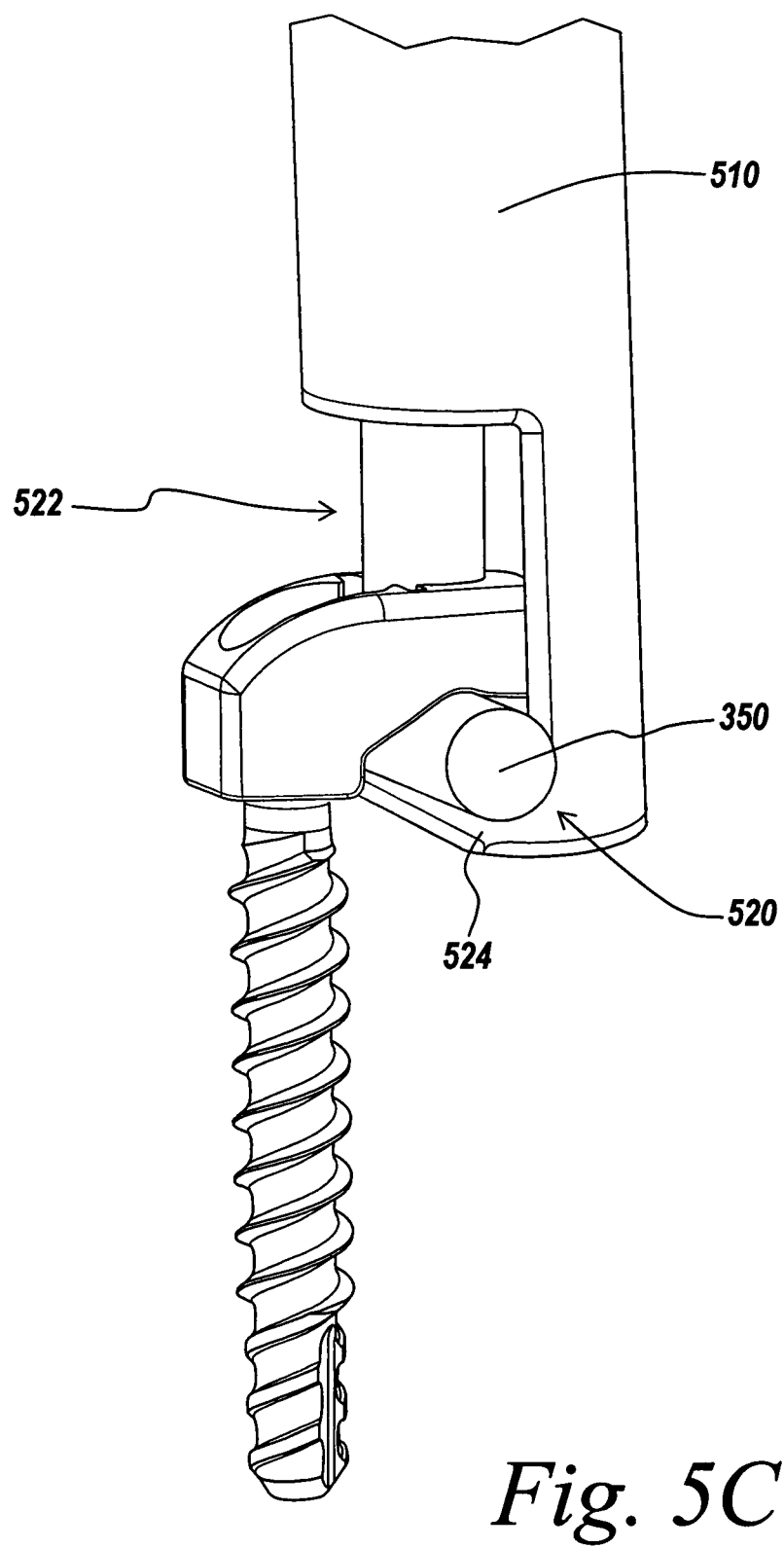

In FIG. 5C, the distal end 520 can be seen in position on the spinal fixation element 350. In this example, the distal end 520 includes a cut-out 522 and a lower ledge 524. The cut-out 522 allows the distal end 520 of the sleeve to be positioned on the spinal fixation element 350. The lower ledge 524 of the distal end is configured to engage the spinal fixation element 350.

Figure 5D:
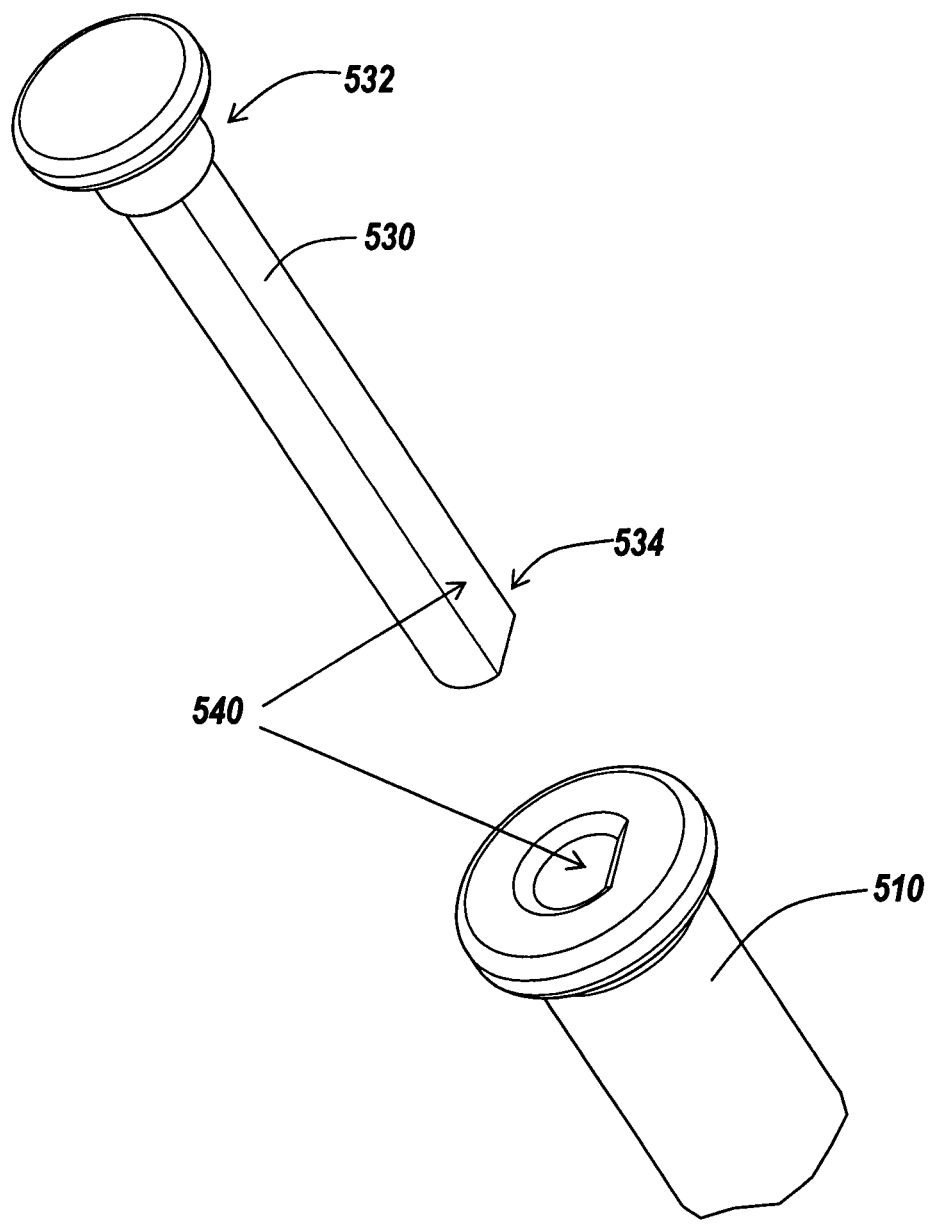
Figure 5E:
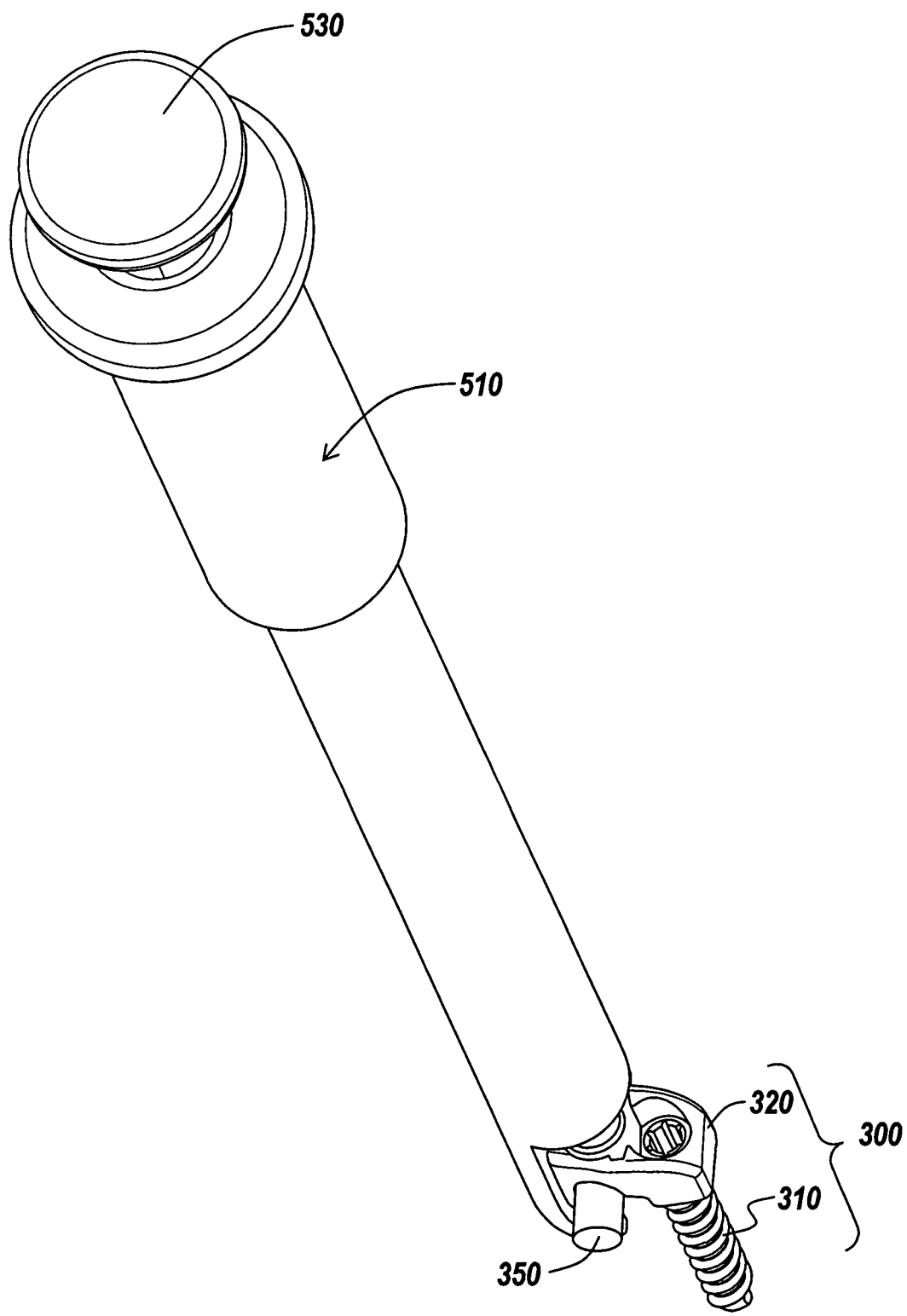

In FIG. 5D the plunger 530 is inserted into the outer sleeve 510. The plunger 530 is configured to fit inside the sleeve 510 and engage the connector body 320 of the implant 300. The plunger includes a proximal end 532 and a distal end 534. In this embodiment, the plunger 530 engages the connector body 320 through the extension shaft 336. In other embodiment, the extension shaft 336 may be removed prior to inserting the plunger 530, wherein the plunger 530 directly engages the connector body 520. In still other embodiments, the plunger 530 may have a lumen (not shown) between the proximal 532 and distal 534 ends allowing the plunger 530 to pass over the extension shaft 336 to directly engage the connector body 320. In certain embodiments, the sleeve 510 and plunger 530 may include and alignment feature 540 or otherwise be keyed to ensure proper alignment of the plunger 530 and sleeve 510.

By pressing down on the plunger 530 while maintaining the position of the sleeve 510, the spinal fixation element 350 is engaged by the connector body 320. In effect, the lower ledge 524 of the distal end 520 of the sleeve 510 applies an upward force on the spinal fixation element 350 while the plunger 530 applies a downward force on the connector body 520 through the extension shaft 336. An example of the spinal fixation element 350 engaged by the connector body 320 inserted by the instrument 500 can be seen in FIG. 5E.

Figure 5F:
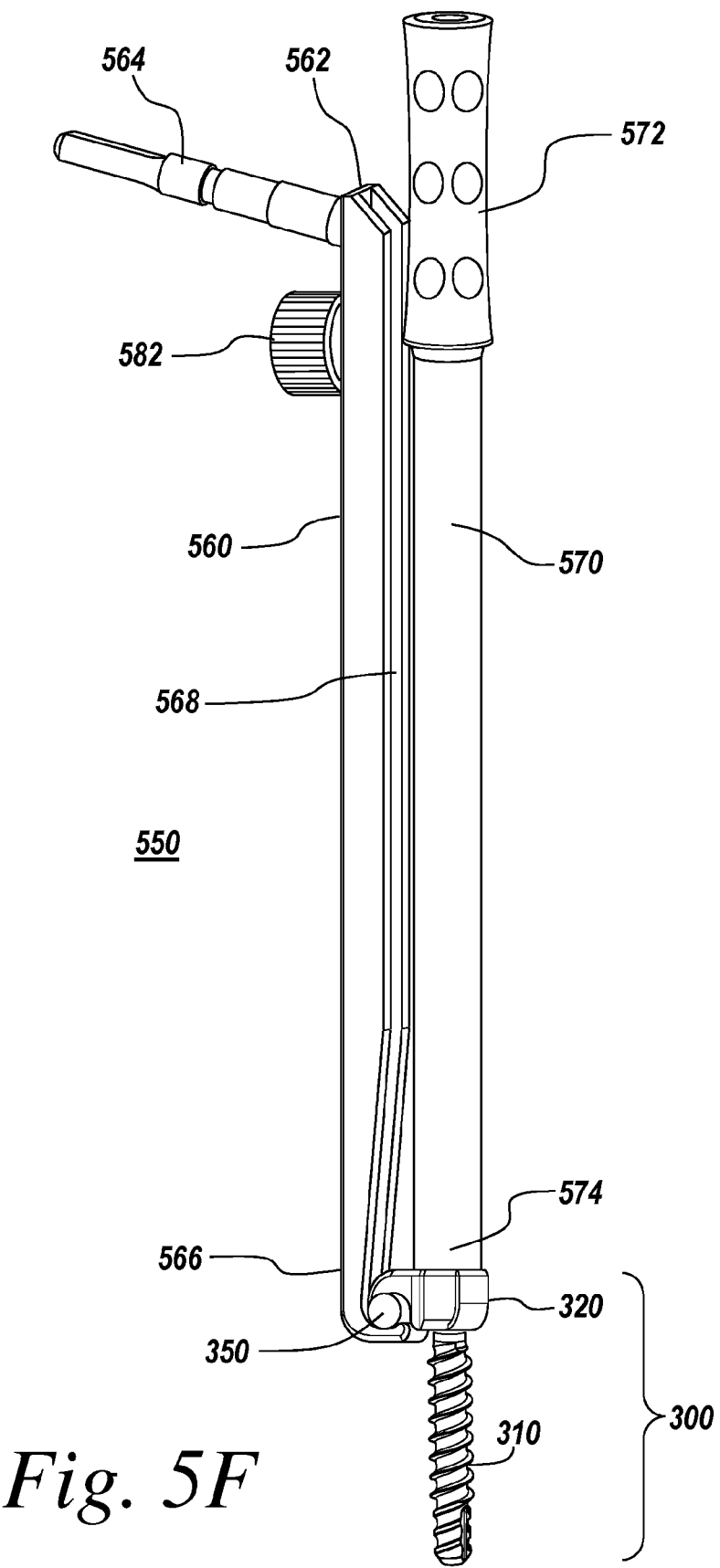
FIGS. 5F-5G illustrate another exemplary embodiment of an instrument for engaging a spinal fixation element with an implant.
Figure 5G:
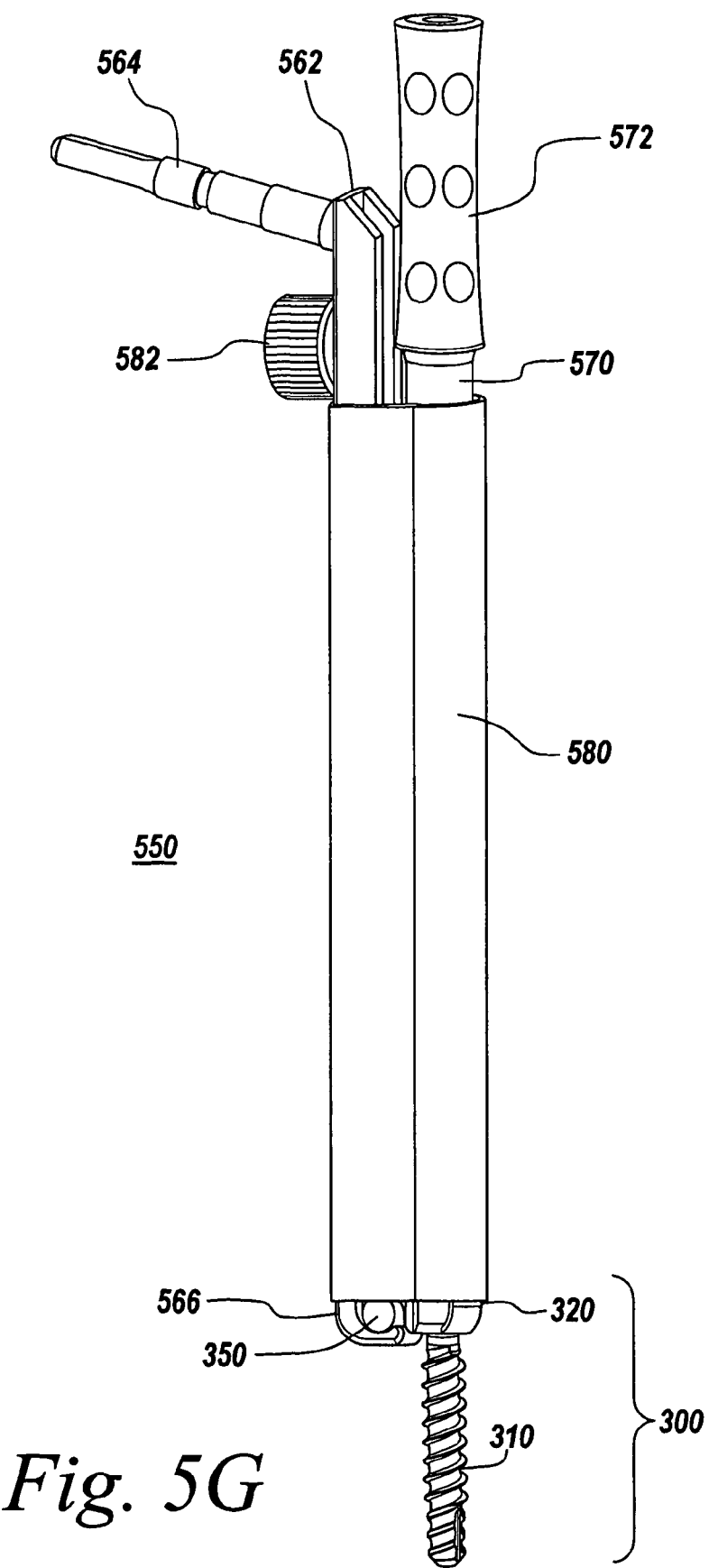

Another embodiment of an instrument 550 is shown in FIGS. 5F and 5G. In this embodiment the sleeve is a half-sleeve 560 and the plunger is an insertion tool 570. This embodiment of the instrument 550 is configured to be used in conjunction with a cannula 580 as shown in FIG. 5G.

The half-sleeve 560 has a proximal end 562, a distal end 566 and a lumen 568 extending between the proximal 562 and distal 566 ends. The distal end 566 is configured to engage the spinal fixation element 350. In this embodiment, the proximal end 562 further includes a handle 564 that can be used to manipulate or secure the position of the half-sleeve 560. The open nature of the half-sleeve 560 allows it to work in conjunction with any number devices for placing a spinal fixation device 350 into the connector body 320.

In the embodiment of FIGS. 5F and 5G, an insertion tool 570 is used as a plunger in conjunction with the half-sleeve 560. The insertion tool 570 has a handle 572 at a proximate end and a distal end 574 for engaging the connector body 320. The insertion tool may be the tool used to place the implant 300, drive the bone anchor 310, or insert the set screw 330. In other embodiments an extension shaft 336 may be used in conjunction with the half sleeve 560.

As mentioned above and shown in FIG. 5G, the half-sleeve 360 and instrument 570 may be sized and dimensioned to be inserted into and used in conjunction with a cannula 580. In certain embodiment, the half-sleeve 560 may include a mechanism, such as a knob 582, for attaching the half-sleeve 560 to the cannula 580. In this example, the knob 580 may be tightened down by the user to secure the cannula 580 to the half-sleeve 560. It should be understood that other suitable mechanisms for securing the half-sleeve 560 to the cannula can be employed.

Once inserted, the half-sleeve 560 and insertion tool 570 are used as the sleeve 510 and plunger 530 described above. By pressing down on the insertion tool 570 while maintaining the position of the half-sleeve 560, the spinal fixation element 350 is engaged by the connector body 320. In effect, the distal end 566 of the half-sleeve 560 applies an upward force on the spinal fixation element 350 while the insertion tool 570 applies a downward force on the connector body 520.

Up to this point, all the embodiments discussed have been configured to be top loaded so as to engage the spinal fixation element from above. However, it should be understood that some embodiment of the implant may be configured to engage a spinal fixation element from the side. An example of this can be seen in FIGS. 6A-6C.

Figure 6A:
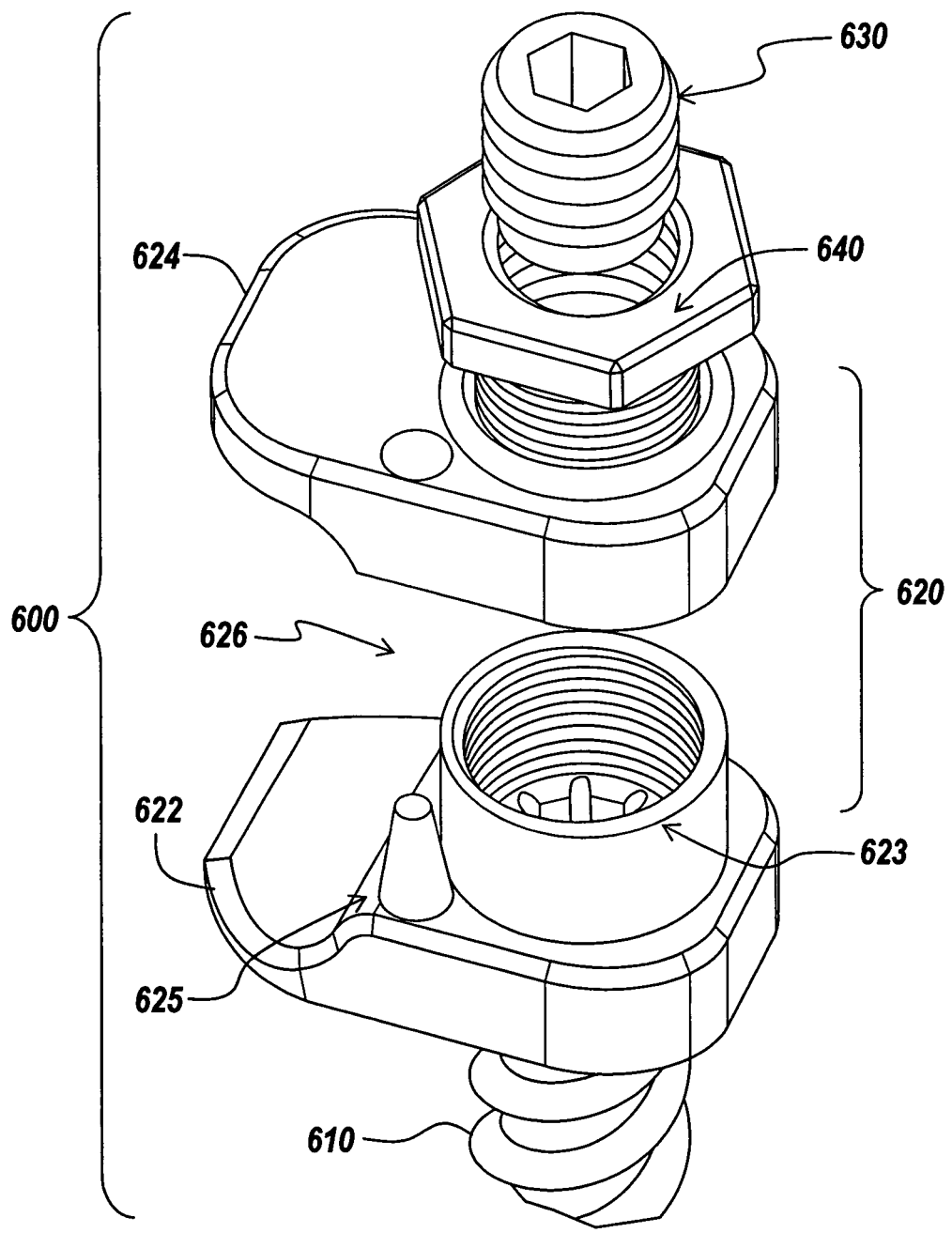
FIGS. 6A-6C illustrate another exemplary embodiment of an implant.
Figure 6B:
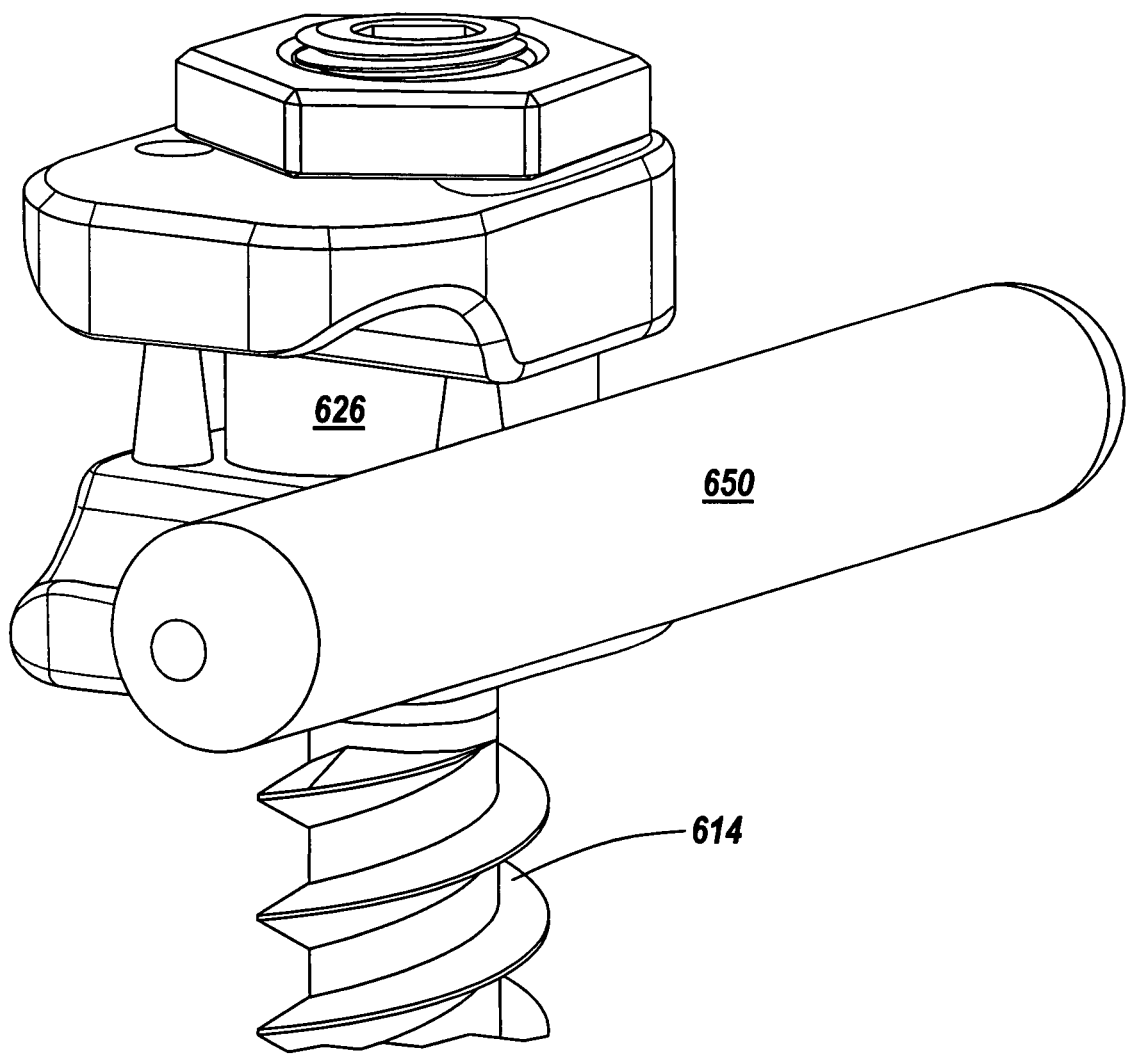
Figure 6C:
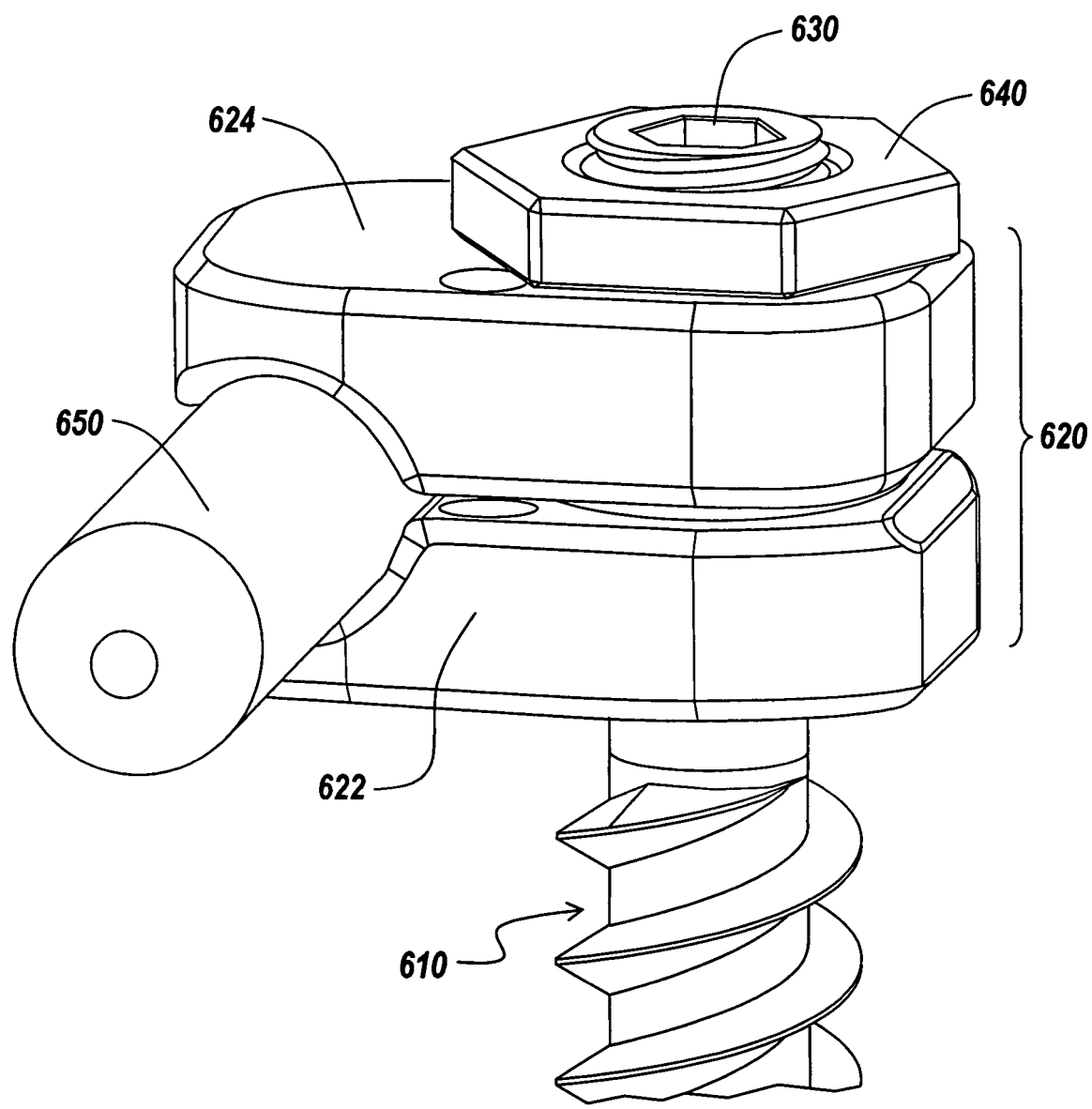

In the embodiment of FIGS. 6A through 6C the implant 600 has a bone anchor 610 and a connector body 620 configured to engage the bone anchor 610 and spinal fixation element 650. In the example depicted in FIGS. 6A through 6C, the bone anchor 610 and connector body 620 are already assembled such that the proximal head of the bone anchor 610 is engaged by the connector body 620 leaving only the distal shaft 614 of the bone anchor 610 visible. The implant 600 also includes a first locking mechanism 630 and a second locking mechanism 640.

In this embodiment, the connector body 620 includes a lower clamp mechanism 622 and an upper clamp mechanism 624 configured to mate with the lower clamp mechanism to engage the spinal fixation element 650. The lower clamp mechanism 622 and upper clamp mechanism 624 further form a cavity 626 for receiving the bone anchor 610.

The lower clamping mechanism includes a main boss 623 and a tapered pin 625. The main boss 623 is configured for mating the upper clamping mechanism 624 to the lower clamping mechanism 622. As such, the upper clamping mechanism 624 rides around the main boss 623. The tapered pin 625 is configured to engage the upper clamping mechanism 624 to restrict the movement of the upper clamping mechanism around the main boss 623.

In this embodiment, the implant 600 is configured to be implanted adjacent to the spinal fixation element 650 such that the spinal fixation element 650 is offset from the longitudinal axis of the distal shaft 614 of the bone anchor 610 as shown in FIG. 6B. The connector body 620 is able to move polyaxially with respect to the bone anchor 610 to engage the spinal fixation element 650. As such, once the bone anchor 610 has been implanted, the connector body 620 can be rotated 90° to engage the spinal fixation element 650. As the connector body 620 is turned, the upper clamping mechanism 624 slides along the main boss 623 and tapered pin 625, allowing the upper clamping mechanism 624 to move apart from the lower clamping mechanism 622, so that the spinal fixation element 650 may be inserted between the upper 624 and lower clamping 622 mechanism thereby being engaged by the connector body 620. An example of this can be seen in FIG. 6C.

Once the spinal fixation element 650 has been engaged by the connector body 620, the spinal fixation element may be secured between the upper 624 and lower 622 clamping mechanism by tightening the second locking mechanism 640. In this embodiment, the second locking mechanism 640 is an outer nut that clamps the upper 624 and lower 622 clamping mechanisms together.

The polyaxial motion of the connector body 620 may be fixed using the first locking mechanism 630. In this example, the first locking mechanism 630 is a set screw configured to engage the bone anchor 610 and connector body 620 to lock their positions relative to each other.

Figure 7A:
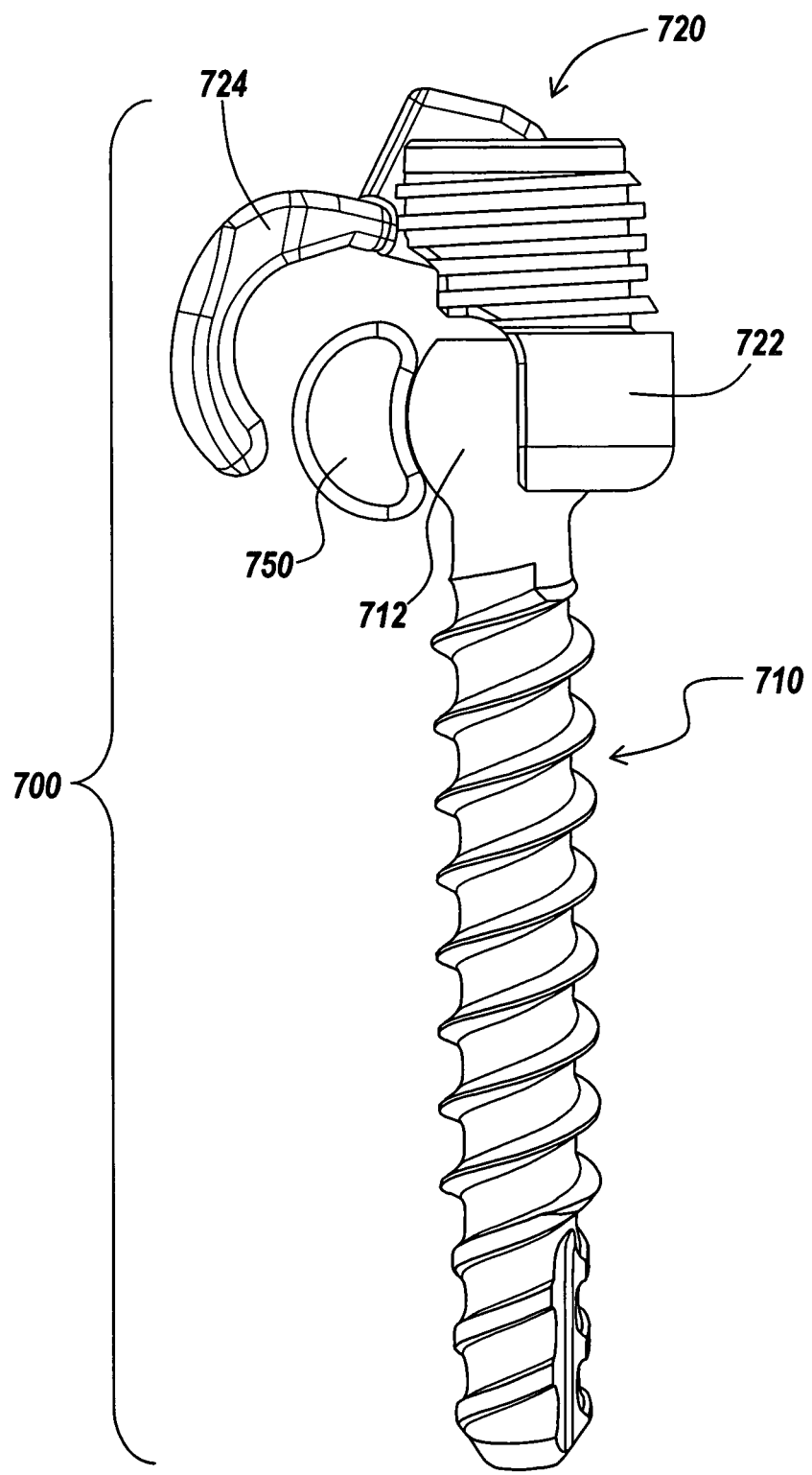
FIGS. 7A-7C illustrate another exemplary embodiment of an implant.
Figure 7B:
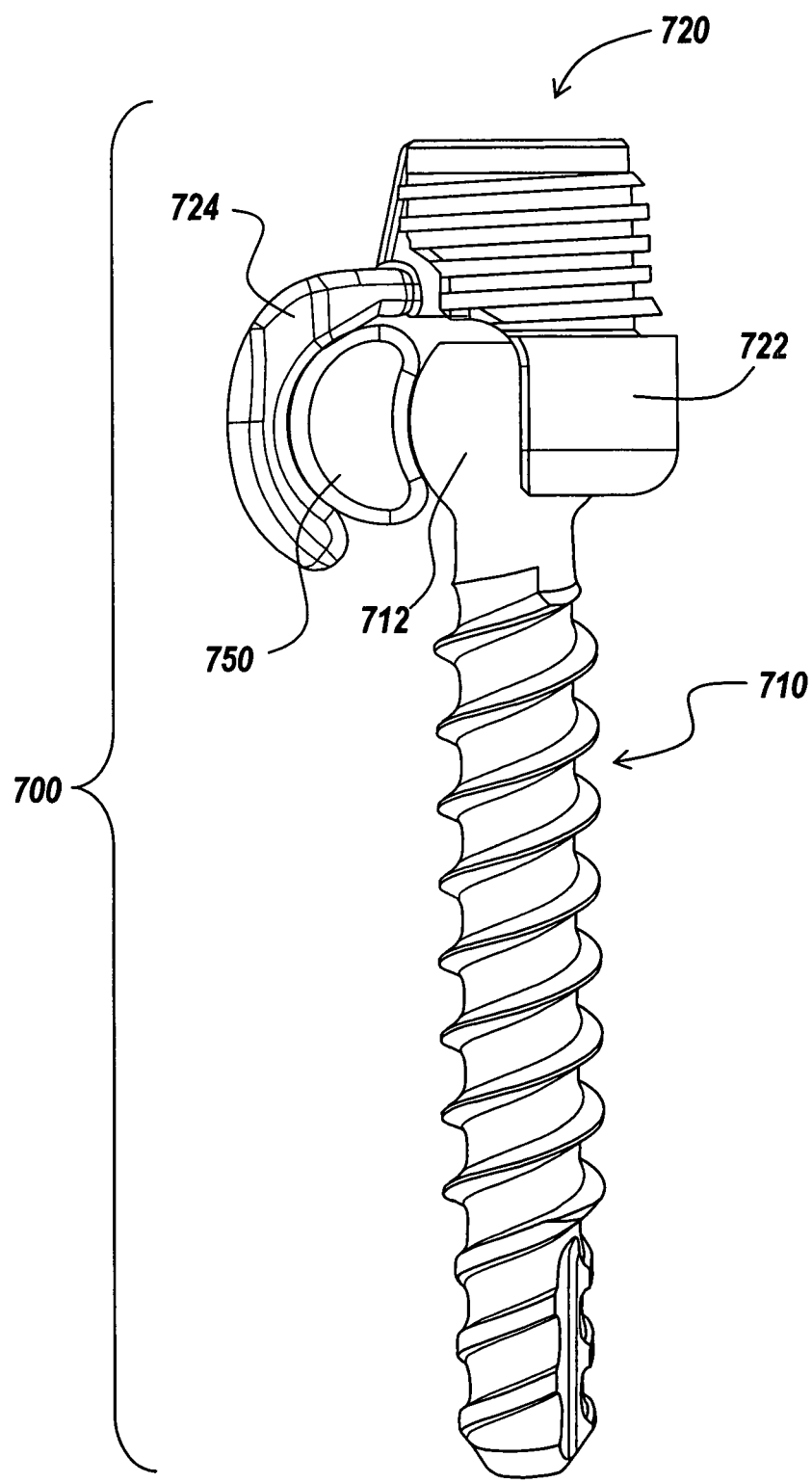
Figure 7C:
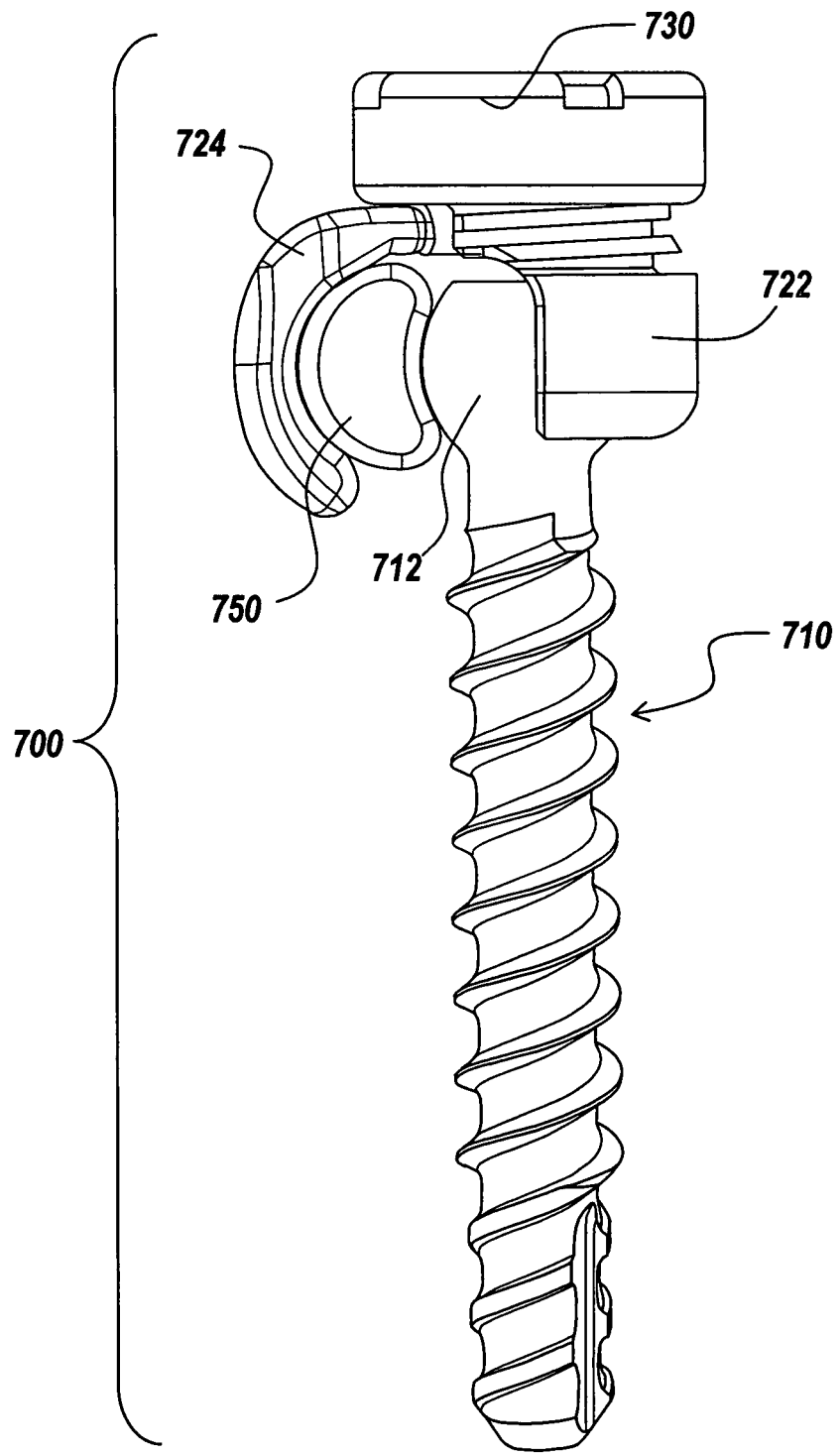

FIGS. 7A-7C depict another embodiment of an implant 700 configured to engage a specially configured spinal fixation element 750. The implant features a bone anchor 710 and a connector body 720. In the example depicted in FIGS. 7A-7C, the bone anchor 710 and connector body 720 are already assembled such that the proximal head 712 of the bone anchor 710 is engaged by the connector body 720. The implant 700 also includes a locking mechanism 730.

In the embodiment of FIGS. 7A-7C, the connector body 720 includes a first half 722 and a second half 724. The first half 722 is configured to engage the proximal head 712 of the bone anchor 710 and mate with the second half 724 to engage the spinal fixation element 750. The first half 722 is pivotably coupled to the second half 724. The two halfs are inserted at the same time. The second half 724 pivots away from the first half 722 allowing the spinal fixation element 750 to mate with the proximal head 712 of the bone anchor 710. An example of this can be seen in FIG. 7A.

The spinal fixation element 750 is configured to engage the proximal head 712 of the bone anchor 710. In this embodiment, the spinal fixation device has a kidney shaped cross section. Other configurations such as an I-beam shape cross section are also possible.

Once the spinal fixation element 750 has engaged the proximal head 712, the second half 724 may be pivoted toward the first half to capture the spinal fixation element 750. An example of this can be seen in FIG. 7B. In some such embodiments, the first half 722 coming together with the second half 724 may have features that may provide audible or tactile feedback indicated the spinal fixation device 750 has be engaged.

By capturing the spinal fixation element 750 with the second half 724, the second half 724 pushes against the spinal fixation element 750. The spinal fixation element pushes against the proximal head 712 of the bone anchor 710. The proximal head 712 is pushed against the first half 722. The position of the connector body 720 and spinal fixation device 750 may then be secured by using locking mechanism 730. An example of this can be seen in FIG. 7C.

Figure 8:
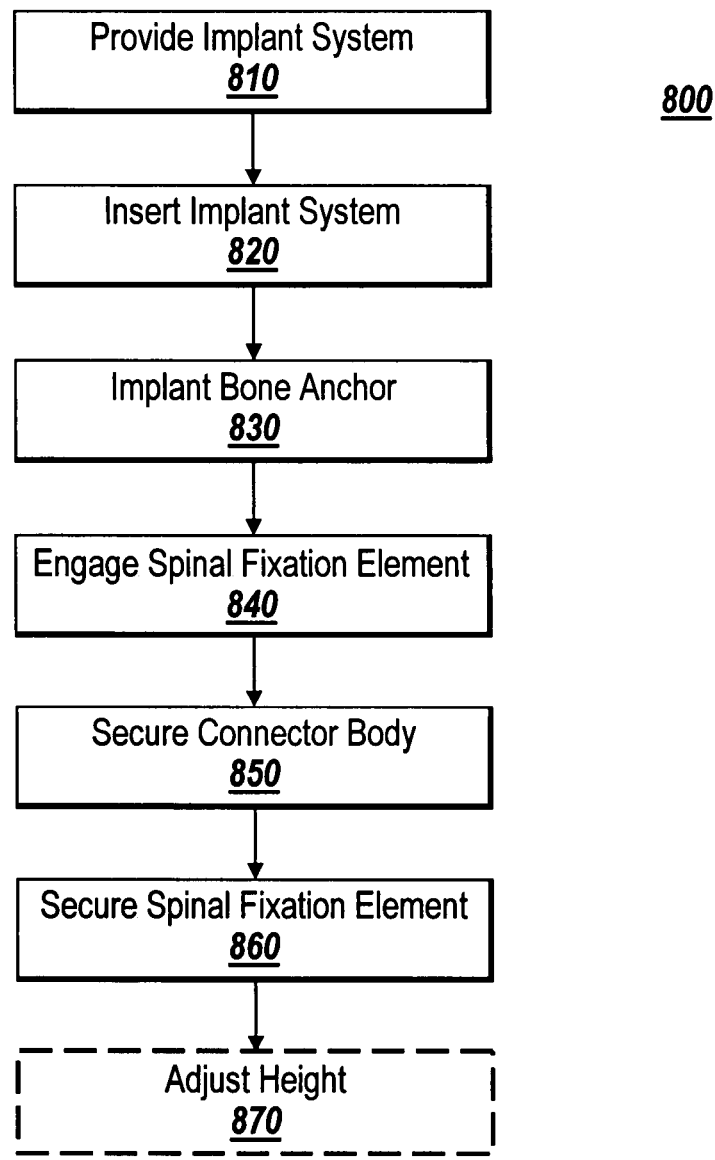
FIG. 8 is a flow diagram of an exemplary embodiment of a method for securing a spinal fixation element using an implant.

FIG. 8 depicts a flow chart 800 for an exemplary method of securing a spinal fixation element that has been previously inserted. The method uses the implant of the present invention (step 810). The implant is then inserted at the surgical site (step 820). The distal shaft of the bone anchor may then be implanted into a vertebra (step 830). Once the bone anchor is implanted, the spinal fixation element (SFE) may be engaged by the connector body of the implant device (step 840). The position of the connector body may then be secured (step 850). Likewise, the implant device may also be secured (step 860). In some embodiment, the implant height may be further adjusted (step 870).

Inserting the implant (step 820) may be performed using any appropriate method, ideally a minimally invasive method, including using a cannula, k-wire, etc. Techniques and instruments for minimally invasive insertion are discussed in detail in the related applications: application DUQ-034 entitled "Minimally Invasive Guide System," application Ser. No. 11/897,642, filed on Aug. 31, 2007, and DUQ-037 entitled "Method and System for Securing a Rod to a Bone Anchor with a Connector," application Ser. No. 11/897,566, now U.S. Pat. No. 8,025,682, filed on Aug. 31, 2007.

Engaging the spinal fixation device with the implant (step 840) may be performed using an instrument as describe in regard to FIGS. 5A-5E or any traditional method including self retaining drivers, cannulas, lateral reduction instruments, etc.

Securing the connector body (step 850) and/or spinal fixation device (step 860) may be preformed using one or more locking members or securing mechanisms in any order as described above in regards to the various discussed embodiments.

A person having ordinary skill in the art will appreciate that the aforementioned methods and devices for securing a spinal fixation element can be modified depending on the type of spinal fixation element or implant being used, as well as the specific procedure being employed. Moreover, other methods and devices known in the art can be used in accordance with the present invention.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

While the instruments and methods of the present invention have been particularly shown and described with reference to the exemplary embodiments thereof, those of ordinary skill in the art will understand that various changes may be made in the form and details herein without departing from the spirit and scope of the present invention. Those of ordinary skill in the art will recognize or be able to ascertain many equivalents to the exemplary embodiments described specifically herein by using no more than routine experimentation. Such equivalents are intended to be encompassed by the scope of the present invention and the appended claims.

The invention claimed is:

1. An implant for use in a minimally invasive spinal fixation, the implant comprising:
    a polyaxial bone anchor having a proximal head and a distal shaft extending along a longitudinal axis configured to engage bone;
    a connector body that moves polyaxially when unlocked and that is configured to engage the proximal head of the bone anchor and engage a spinal fixation element offset from the longitudinal axis of the bone anchor shaft,
    wherein the connector body comprises a slot to receive the spinal fixation element, the slot being open toward an end of the distal shaft so that the spinal fixation element is received in the slot in a direction from the distal shaft to the proximal head;
    wherein the connector body is configured to couple the spinal fixation element to the bone anchor so that a topmost portion of the spinal fixation element oriented proximally is surrounded by the connector body while a bottommost portion of the spinal fixation element oriented distally is not surrounded by the connector body and said bottommost portion lacks support underneath so that the implant is suitable for use in a rod first procedure; and
    an integrated securing mechanism comprising a structure integrated in the connector body in the slot to secure a position of the spinal fixation element in the slot;
    a set screw contacting the bone anchor to secure positions of the bone anchor relative to the connector body so as to lock polyaxial motion of the bone anchor and polyaxial motion of the connector body and to secure a position of the spinal fixation element by pushing the securing mechanism against the spinal fixation element.

2. The implant of claim 1, wherein the connector body is pivotable around the proximal head of the bone anchor.

3. The implant of claim 1, wherein the set screw comprises a pass-through feature allowing the bone anchor to be engaged after the locking member has been inserted.

4. The implant of claim 1, wherein the connector body further comprises snap on features for providing feedback to a user indicating the connector body has engaged the spinal fixation element.

5. The implant of claim 1, wherein the connector body comprises:
    a cavity for receiving the proximal head of the bone anchor; and
    a hook for receiving the spinal fixation element.

6. The implant of claim 5, wherein the hook is deformable to engage the spinal fixation element with a snap fit.

7. The implant of claim 1, further comprising an engagement tool for engaging the spinal fixation device with connector body, the engagement tool comprising:
    a sleeve having a proximal end, a distal end configured to engage the spinal fixation element, and a lumen extending between the proximal and distal ends; and
    a plunger configured to fit inside the sleeve and engage the connector body;
    wherein inserting the plunger into the sleeve to engage the connector body causes the connector body to engage the spinal fixation element engaged by the sleeve.

8. The implant of claim 7, wherein the sleeve and plunger of the instrument are keyed to provide proper alignment of the plunger inside the sleeve.

9. The implant of claim 7, wherein the sleeve comprises a half-sleeve.

10. The implant of claim 7, wherein the plunger comprises an insertion tool.

* * * * *